(12) United States Patent
Zurn

(10) Patent No.: US 8,663,209 B2
(45) Date of Patent: Mar. 4, 2014

(54) VESSEL CLEARING APPARATUS, DEVICES AND METHODS

(76) Inventor: William Harrison Zurn, Sunnyvale, CA (US)

( * ) Notice: Subject to any disclaimer, the term of this patent is extended or adjusted under 35 U.S.C. 154(b) by 0 days.

(21) Appl. No.: 13/356,884

(22) Filed: Jan. 24, 2012

(65) Prior Publication Data

US 2013/0190752 A1    Jul. 25, 2013

(51) Int. Cl.
  *A61B 18/18*    (2006.01)
(52) U.S. Cl.
  USPC ............... 606/10; 606/7; 607/88; 600/427
(58) Field of Classification Search
  USPC ..................... 606/10, 7; 607/88; 600/427
  See application file for complete search history.

(56) References Cited

U.S. PATENT DOCUMENTS

| | | | |
|---|---|---|---|
| 3,657,744 A | 4/1972 | Ersek |
| 4,061,134 A | 12/1977 | Samuels et al. |
| 4,140,126 A | 2/1979 | Choudhury |
| 4,276,874 A | 7/1981 | Wolvek et al. |
| 4,560,374 A | 12/1985 | Hammerslag |
| 4,617,932 A | 10/1986 | Kornberg |
| 4,650,466 A | 3/1987 | Luther |
| 4,654,024 A | 3/1987 | Crittenden et al. |
| 4,655,771 A | 4/1987 | Wallsten |
| 4,672,961 A | 6/1987 | Davies |
| 4,728,328 A | 3/1988 | Hughes et al. |
| 4,732,152 A | 3/1988 | Wallsten et al. |
| 4,739,762 A | 4/1988 | Palmaz |
| 4,787,899 A | 11/1988 | Lazarus |
| 4,795,458 A | 1/1989 | Regan |
| 4,819,632 A | 4/1989 | Davies |
| 4,830,003 A | 5/1989 | Wolff et al. |
| 4,892,539 A | 1/1990 | Koch |
| 4,913,141 A | 4/1990 | Hillstead |
| 4,954,126 A | 9/1990 | Wallsten |
| 4,969,896 A | 11/1990 | Shors |
| 4,994,071 A | 2/1991 | MacGregor |
| 4,998,539 A | 3/1991 | Delsanti |
| 4,998,972 A | 3/1991 | Chi et al. |
| 5,024,671 A | 6/1991 | Tu |
| 5,026,377 A | 6/1991 | Burton et al. |
| 5,035,706 A | 7/1991 | Giantureo et al. |
| 5,047,050 A | 9/1991 | Arpesani |
| 5,078,726 A | 1/1992 | Kreamer |

(Continued)

OTHER PUBLICATIONS

Andrew Bridges, FDA: Heart Stents Don't Up Risk of Death, Associated Press, Dec 7, 2006.

(Continued)

*Primary Examiner* — Bill Thomson
*Assistant Examiner* — Sebastian X Lukjan
(74) *Attorney, Agent, or Firm* — Law Office of Alan W. Cannon

(57) ABSTRACT

A clearing module is provided that includes a main body configured and dimensioned to be received within a vessel or duct of a patient, adjacent a surgical target area in the patient. The main body includes: an instruction receiving unit configured to receive wireless instructions from an instruction transmitter located outside the patient's body while the module is located inside of the patient's body; a positioning element configured to be monitored by a system external of the patient's body while the positioning element is inside the patient's body; and a destructive energy emitter configured to emit destructive energy from the module toward the surgical target area according to instructions received from the instructions receiving unit.

18 Claims, 9 Drawing Sheets

(56) References Cited

U.S. PATENT DOCUMENTS

| | | | |
|---|---|---|---|
| 5,084,065 A | 1/1992 | Weldon | |
| 5,090,959 A | 2/1992 | Samson et al. | |
| 5,100,426 A | 3/1992 | Nixon | |
| 5,102,417 A | 4/1992 | Palmaz | |
| 5,104,399 A | 4/1992 | Lazarus | |
| 5,104,404 A | 4/1992 | Wolff | |
| 5,122,154 A | 6/1992 | Rhodes | |
| 5,123,917 A | 6/1992 | Lee | |
| 5,158,548 A | 10/1992 | Lau | |
| 5,192,297 A | 3/1993 | Hull | |
| 5,201,757 A | 4/1993 | Heyn et al. | |
| 5,207,695 A | 5/1993 | Trout, III | |
| 5,219,355 A | 6/1993 | Parodi et al. | |
| 5,275,622 A | 1/1994 | Lazarus et al. | |
| 5,282,824 A | 2/1994 | Gianturco | |
| 5,316,023 A | 5/1994 | Palmaz et al. | |
| 5,360,443 A | 11/1994 | Barong et al. | |
| 5,395,334 A | 3/1995 | Keith et al. | |
| 5,397,345 A | 3/1995 | Lazarus | |
| 5,489,295 A | 2/1996 | Piplani et al. | |
| 5,562,728 A | 10/1996 | Lazarus | |
| 5,609,625 A | 3/1997 | Piplani | |
| 5,628,783 A | 5/1997 | Quiachon | |
| 5,662,700 A | 9/1997 | Lazarus | |
| 5,669,936 A | 9/1997 | Lazarus | |
| 5,741,246 A | 4/1998 | Prescott | |
| 5,824,015 A | 10/1998 | Sawyer | |
| 5,830,209 A | 11/1998 | Savage et al. | |
| 5,855,599 A | 1/1999 | Wan | |
| 5,951,566 A | 9/1999 | Lev | |
| 6,004,269 A | 12/1999 | Crowley et al. | |
| 6,019,784 A | 2/2000 | Hines | |
| 6,027,863 A | 2/2000 | Donadio, III | |
| 6,033,398 A | 3/2000 | Farley et al. | |
| 6,074,374 A | 6/2000 | Fulton | |
| 6,107,004 A | 8/2000 | Donadio, III | |
| 6,139,511 A | 10/2000 | Millet | |
| 6,146,814 A | 11/2000 | Huter et al. | |
| 6,168,579 B1 | 1/2001 | Tsugita | |
| 6,203,732 B1 | 3/2001 | Clubb et al. | |
| 6,210,362 B1 | 4/2001 | Ponzi | |
| 6,241,745 B1 | 6/2001 | Rosenthal | |
| 6,251,128 B1 | 6/2001 | Knopp et al. | |
| 6,374,476 B1 | 4/2002 | Ponzi et al. | |
| 6,398,792 B1 | 6/2002 | O'Connor | |
| 6,520,934 B1 | 2/2003 | Lee et al. | |
| 6,524,303 B1 | 2/2003 | Garibaldi | |
| 6,620,148 B1 | 9/2003 | Tsugita | |
| 6,673,104 B2 | 1/2004 | Barry | |
| 6,696,335 B2 | 2/2004 | Bonart | |
| 6,786,896 B1 | 9/2004 | Madhani et al. | |
| 6,926,670 B2 | 8/2005 | Rich et al. | |
| 6,968,743 B2 | 11/2005 | Rich et al. | |
| 6,980,843 B2 | 12/2005 | Eng et al. | |
| 6,998,358 B2 | 2/2006 | French et al. | |
| 7,242,301 B2 | 7/2007 | August et al. | |
| 7,607,440 B2 | 10/2009 | Coste-Maniere et al. | |
| 7,647,831 B2 | 1/2010 | Corcoran et al. | |
| 7,699,059 B2 | 4/2010 | Fonseca et al. | |
| 7,751,869 B2 * | 7/2010 | Rioux et al. | 600/427 |
| 7,839,153 B2 | 11/2010 | Joy et al. | |
| 7,899,578 B2 | 3/2011 | Prisco et al. | |
| 7,907,166 B2 | 3/2011 | Lamprecht et al. | |
| 7,967,754 B2 | 6/2011 | Knight | |
| 7,979,108 B2 | 7/2011 | Zurn | |
| 2002/0133219 A1 | 9/2002 | Barry | |
| 2005/0159802 A1 | 7/2005 | Furst et al. | |
| 2006/0224154 A1 | 10/2006 | Shadduck et al. | |
| 2006/0232417 A1 | 10/2006 | August et al. | |
| 2007/0010702 A1 | 1/2007 | Wang et al. | |
| 2007/0135887 A1 | 6/2007 | Maschke | |
| 2007/0167702 A1 | 7/2007 | Hasser et al. | |
| 2007/0210786 A1 | 9/2007 | Allen et al. | |
| 2008/0004595 A1 | 1/2008 | Viswangthan et al. | |
| 2008/0021307 A1 | 1/2008 | Freeman et al. | |
| 2009/0005859 A1 | 1/2009 | Keilman | |
| 2009/0062639 A1 * | 3/2009 | Zurn | 600/410 |
| 2009/0247911 A1 * | 10/2009 | Novak et al. | 601/2 |
| 2011/0040177 A1 | 2/2011 | Zurn | |
| 2011/0257562 A1 * | 10/2011 | Schaer | 601/2 |
| 2011/0307034 A1 * | 12/2011 | Hastings et al. | 607/61 |

OTHER PUBLICATIONS

Andrew Bridges, FDA: Stent Patients Face Blood Clot Risk, Associated Press, Dec 5, pp. 1-3, 2006.

A. Kastalsky, et al., Semiconductor high-energy radiation scintillation detector, pp. 650-656, 2006.

Atomic and Molecular Manipulation to Drive Development of Nanoscience, pp. 1-2, Jun. 2011.

Bonanomi., et al., Microelectromechanical systems for endoscopic cardiac surgery. 2003, vol. 126, No. 3, pp. 851-852.

Cordes, et al., CMOS cameras allow robut active stabilization of laser beams. Aug. 2011, pp. 73-76.

Chatterjee., Contributing Technical Editor. New devices for nanoelectronics., Mar. 3, 2011, pp. 18.

CAT Scan (CT)—Body, download Mar. 19, 2009, pp. 1-6. http://www.radiologyinfo.org/en/info.cfm?PG=bodyct.

Edamatsu, Entangled Photons: Generation, Observation, and Characterization. vol. 46, No. 11. 2007, pp. 7175-7187.

Engineering a Paradigm Shift in At-Home Monitoring Devices. Jun. 2011, pp. 4 & 6.

Edwards, et al., CT measurement of main pulmonary artery diameter, 1998, pp. 1018-1020.

Frank J. Veith, M.D., The Rush to Stent: A Cause for Concern, VascularWeb, Provided by the Society for Vascular Surgery, vol. 2—2006 Issue 2.

Frank J. Criado, MD, Ronald M. Fairman, MD, and Gary J. Becker, MD, Talent LPS AAA stent graft: Results of a pivotal clinical trial, Journal of Vascular Surgery vol. 37, No. 4 , 2006.

Grace, et al., Why MEMS-based systems solutions? Significant reasons have caused MEMS suppliers to change their design approach, thus opening new market opportunities. 2011, pp. 17-19.

Gilleo_MEMS_in-Medicine_August_2005_pp_1_3_pp_1_10.

Hank Russell, CT Angiography Shows Promise in Arterial Imaging, VascularWeb, Provided by the Society for Vascular Surgery, vol. 2—2006 Issue 1.

Hank Russell, Imaging System Tested for Visualizing Stents, VascularWeb, Provided by the Society for Vascular Surgery, vol. 2—2006 Issue 1.

Hecht, The incredible shrinking laser makers a big impact. Oct. 2011, pp. 41-45.

Jeff Evans, AAA Repair: Early Intervention or Wait and See?, VascularWeb,Provided by the Society for Vascular Surgery ,vol. 2—2006 Issue 3.

Jayaraman, et al., 760 kHz OCT scanning possible with MEMS-tunable VCSEL. 2011, pp. 1-2.

John Carey, No One Wanted to Hear, Business Week, Oct. 9, 2006, pp. 91-92.

Karen M. Dente, M.D., Endovascular Repair for Aneurysm Rupture, VascularWeb, Provided by the Society for Vascular Surgery, vol. 2—2006 Issue 1.

Kiourti., Biomedical Telemetry: Communication Between Implanted Devices and the External World. 2010, pp. 1-7.

Kotzar, et al., Evalution of MEMS materials of construction for implantable medical devices. 2002, pp. 2737-2750.

MEMS in medical devices: the possibilities are endless. 2009, ppl 1-2.

Mark S. Lesney, Aortic Debranching Can Aid Endovascular Repair of TAA, VascularWeb, Provided by the Society for Vascular Surgery, vol. 2—2006 Issue 2.

Seward., Fantastic voyage through the cardiovascular system. 2004, 5, pp. 8-11.

Timothy F. Kim, European Series: Carotid Stent vs. Endarterectomy, VascularWeb,Provided by the Society for Vascular Surgery ,vol. 2—2006 Issue 3.

(56) References Cited

OTHER PUBLICATIONS

Timothy F. Kim, Endovascular Aortic Repair Less Harmful to Heart?, VascularWeb, Provided by the Society for Vascular Surgery, vol. 2—2006 Issue 3.

Timothy F. Kim, Endovascular AAA Repair Is Gaining, Expert Asserts, VascularWeb, Provided by the Society for Vascular Surgery, vol. 1—2005 Issue 2.

Timothy F. Kim, Endovascular Emergency Repair of Ruptured AAA Uses Balloon Technique, Vascular Web, Provided by the Society for Vascular Surgery, vol. 2—2006 Issue 3.

Y. Joseph Woo, MD, Acute Aortic Dissection: A Case for Specialized Centers Colleague Commentary, VascularWeb, Provided by the Society for Vascular Surgery, vol. 2—2006 Issue 3.

Weiler., High-power pico- and femtosecond lasers enable new applications. Oct. 2011, pp. 55-61.

Zimmermann, Michael M.D., Ph.D.; Krishnan, René M.D.; Raabe, Andreas M.D., Ph.D.; Seifert, Volker M.D., Ph.D., Robot-assisted Navigated Neuroendoscopy, Neurosurgery: vol. 51(6) Dec. 2002 pp. 1446-1452.

Scintillator Image, http://universe-review.ca/I08-24-scintillator.jpg, Jun. 21, 2007.

"How They Work", http://www.upei.ca/~phys221/MH/how_they_work/_how_they_work_.html, Jun. 21, 2007.

CT Scan Equipment Image, http://images.search.yahoo.com/search/images/view?frame=top&back=http%3A%2F%2F%2Fs, Jun. 22, 2007.

Macneil, "Stenting or Open Repair? EVAR, DREAM Trials Inconclusive", VascularWeb, Provided by the Society for Vascular Surgery, vol. 2—2006, Issue 1.

Parker et al., "Pixellated NaI(T1) for Enhanced Performance", Saint-Gobain Ceramics and Plastics, Inc., 2001.

Reichenspurner et al., "Use of the Voice-Controlled and Computer-Assisted Surgical System Zeus for Endoscopic Coronary Artery Bypass Grafting", Journal of Thoracic and Cardiovascular Surgery, vol. 118, Issue 1, Abstract, Jul. 1999.

\* cited by examiner

VESSEL CLEARING APPARATUS, DEVICES AND METHODS

FIELD OF THE INVENTION

The present invention relates, in general, to the field of medical devices and, more particularly, to apparatus and devices for treating the human body vessel system.

BACKGROUND OF THE INVENTION

The mammalian vessel system includes a number of sub-division systems; circulatory, lymph, gastrointestinal tract and urinary system.

The circulatory system is an organ system that passes nutrients (such as amino acids, electrolytes and lymph), gases, hormones, blood cells, etc. to and from cells in the body to help fight diseases and help stabilize body temperature and pH to maintain homeostasis. The circulatory system may be defined as a blood distribution network, but may be considered as composed of the cardiovascular system, which distributes blood, and the lymphatic system, which distributes lymph. While humans, as well as other vertebrates, have a closed cardiovascular system; some invertebrate groups have an open cardiovascular system.

Two types of fluids move through the circulatory system: blood and lymph. The blood, heart, and blood vessels are components of the cardiovascular system. The lymph, lymph nodes, and lymph vessels are components of the lymphatic system. The cardiovascular system and the lymphatic system collectively make up the circulatory system.

The gastrointestinal tract refers to the stomach and intestine, and sometimes to all the structures from the mouth to the anus. (The "digestive system" is a broader term that includes other structures, including the accessory organs of digestion). The tract may also be divided into foregut, midgut, and hindgut, reflecting the embryological origin of each segment of the tract. The GI tract discharges hormones as to help control the digestion process. These hormones, including gastrin, secretin, cholecystokinin, and grehlin, are mediated through either intracrine or autocrine mechanisms, distinguishing that the cells releasing these hormones are conserved structures throughout evolution.

One of the main organs of the urinary system is the kidney. This is important because the kidneys' main role is to filter water-soluble waste products from the blood. The other attachment of the kidneys is at their functional endpoints the ureters, which lies more medial and runs down to the trigone of urinary bladder.

The systems of vessels in the body are important in that, among other functions, they remove toxins from the body and distribute important materials to vital areas of the body. When vessels become blocked or restricted, major problems may occur. For example, a blockage (or partial blockage) of a coronary artery may lead to coronary infarction, a blockage (or partial blockage) of a ureter may lead to kidney damage, a blockage (or partial blockage) of a cerebral vessel may cause a stroke, etc.

Angioplasty surgery has been performed for many years; the accepted surgical procedure of clearing arteries or veins by the use of drugs and devices has been constantly refined. Even so, the fatality rates for patients enduring the surgery still have serious consequences. One reason for the high fatality rate is that the procedure presents a significant surgical endeavor, making it enormously discretionary in-patients with severe coronary problems, in poor health or very old.

With regard to angioplasty, there are currently many different types of medical devices and techniques that are used to perform angioplasty procedures. These devices may include elements such as: tubes, wires, miniaturized devices, devices with heaters, devices with optical fibers, laser energy, rings catheters, balloons, etc. Angioplasty has come to include all customs of vascular interventions typically performed in a minimally invasive or percutaneous environment.

Prior art related to angioplasty include procedures utilizing empty and collapsed balloons on a guide wire, known as a balloon catheter. This type of device is passed into a narrowed location of a vessel and then inflated to an expanded size using water pressures some 75 to 500 times normal blood pressure (6 to 20 atmospheres). Upon expanding, the balloon crushes the features causing the narrowing (e.g., fatty deposits, plaque), thereby opening up the blood vessel for improved flow, and the balloon is then collapsed and withdrawn.

U.S. Pat. No. 4,650,466 to Luther describes an angioplasty device inclusive of a woven tube of metal or plastic fibers and a retraction stylet that are attached at one end to a catheter tube for insertion into a vein, artery and the like for the removal of plaque and similar material. One or more guide wires may be attached to the woven tube for rotation and a maneuver inside the artery. When the guide wires are retracted, the woven tube expands and contacts the interior, plaque-coated wall of the artery. Movement of the guide wires enlarge the woven tube and will remove the atherosclerotic plaque from the artery to form particles, which are trapped within the tube. An expandable fabric within the woven tube that opens and closes with the corresponding expansion and closure of the woven tube may be used to collect the trapped particles. Luther indicates that removal of the angioplasty device from the artery will then remove the atherosclerotic material from the vein, artery or other type of vessel.

U.S. Pat. No. 4,672,961 to Davies discloses a device adapted to be inserted into a coronary artery and vessels for removing plaque deposits within the artery, a guide wire and a flexible tube. Davies further describes an apparatus and procedure for retrolasing plaque deposits in a coronary artery to remove plaque, a device including a tip assembly on the end of a flexible inner tube retaining optical fibers that are slidable along a guide wire. The tip assembly includes a reflective surface rearwardly of a front face that directs laser energy supplied through the optical fibers in a rearward direction through a window portion to a focal point externally of the tip assembly. The deposit is removed as the tip assembly is moved in a rearward progression back through the deposit.

U.S. Pat. No. 4,654,024 to Crittenden et al. discloses a thermorecanalization catheter and method for use in an angioplasty procedure. The catheter disclosed has a heater fixed on its distal end that is used to melt atherosclerotic plaque to clear an obstruction within an artery. The catheter heater is a tapering cone that discharges heat from its outer, leading edges. In use a guidewire is placed into the lumen of the catheter so that the distal tip of the guidewire extends a few centimeters farther into the heater tip. The catheter is conducted into the appropriate coronary branch by way of the guidewire and the wire is advanced until it meets the impediment. Crittenden et al. further suggests the device is advanced over the wire until the heater contacts the plaque. The heater is then employed and the catheter is advanced as the plaque melts.

U.S. Pat. No. 4,819,632 to Davies discloses a retrolasing catheter and method for retrolasing plaque residue in an artery. The apparatus includes a tip assembly on the end of a flexible inner tube containing optical fibers that are slidable along a guide wire. The tip assembly includes a reflective surface rearwardly of a front face that directs laser energy supplied through the optical fibers in a rearward direction through a window portion to a focal point externally of the tip assembly. The residue is removed as the tip assembly is moved in a rearward progression back through the residue.

Nixon, in U.S. Pat. No. 5,100,426 discloses a catheter for executing an atherectomy operation to remove plaque from an artery. The catheter contains a plaque cutting head having an outer shell of thin flexible substance generally cylindrical in cross-section and shaped to engage plaque in an artery. The outer shell has a plurality of openings through which the plaque will enter the shell as the shell is forced against the plaque. A cutter rotates inside the shell to cut the plaque that enters into the shell into small pieces as the catheter is pushed through an artery. A motor drive elongated drive shaft whirls the cutter.

U.S. Pat. No. 5,741,246 to Prescott discloses an apparatus for application of low level laser energy to a concerned vessel following a balloon angioplasty procedure. The apparatus employs a catheter to be inserted into a vessel, such as an artery. An inflatable balloon surrounds a portion of the catheter neighboring a distal end of the catheter. The catheter is coupled to a tube which provides inflation fluid for inflating the balloon. A malleable pleated sleeve of clear silicone would encompass the balloon. Electrically conductive flexible film strips are embedded in the sleeve. The strips are aligned longitudinally along the outside of the balloon. The strips contain a plurality of vertical cavity lasers connected in series. Power is provided to the lasers via an external power source so that each VCSEL emits approximately 1 to 10 milliwatts of power.

U.S. Pat. No. 6,168,579 to Tsugita describes a filter flush system for transitory placement of a filter in an artery or vein. The system generally includes a guidewire that is inserted within a guiding catheter, which has an occlusion balloon disposed about its distal end. The guidewire has an expandable filter, which can be collapsed to pass through a lumen and distal port of the guiding catheter. A lumen is adapted to receive a variety of endovascular devices, including angioplasty, atherectomy, and stenting catheters. Fluid medium or blood can be infused through the lumen of the guiding catheter to flush embolic material or mobile plaque generated during the endovascular procedures toward the expanded filter deployed downstream from the region of interest.

U.S. Pat. No. 6,241,745 to Rosenthal describes a surgical apparatus and a method to reinstate blood flow capacity to occluded and fractionally occluded arterial vessels. An endarterectomy instrument and associated method are provided. The instrument combines a separation ring with a wire loop at the distal end of a resilient, flexible catheter. The separation ring separates the plaque and the inner wall from a segment of an occluded artery. The wire loop is then constricted around the undesired material. The wire loop of the endarterectomy instrument is used to sever, snare and remove the separated inner arterial wall with the occlusion. The wire loop of the endarterectomy instrument is heated by passing a current through in order to sever the undesired material from the arterial wall. The undesired occlusion is removed along with the inner layers of the artery by snaring the material with the wire loop and removing the instrument from the vessel in a single step.

O'Connor in U.S. Pat. No. 6,398,792 discloses an angioplasty catheter with transducer using a balloon for focusing of ultrasonic energy for the procedure. The catheter is inserted into an artery having deposits of plaque and/or thrombus. The catheter includes, at its distal end, an ultrasonic transducer and a dilatation balloon surrounding the transducer such that when the balloon is positioned in the artery adjacent the deposits and inflated, energizing of the ultrasonic transducer will focus the ultrasonic energy against the deposits to cause dissolution of the thrombus into microscopic particles and cause cracking and softening of the plaque. O'Connor further describes the provision of a second ultrasonic transducer as a means for viewing the treatment site, and a second balloon to cooperate with the first balloon to define a chamber between the balloons and with a lumen and a port connected to the chamber to remove any debris of larger than microscopic size which might otherwise tend to move downstream and cause further obstructions. Also described is the use of an expandable filtering device distal of the dilatation balloon for trapping such particles. Subsequent to the ultrasonic radiation of the deposits, the dilatation balloon can be further inflated to force a stent into the wall of the artery.

In U.S. Pat. No. 6,620,148, Tsugita describes a filter flush system for transitory placement of a filter in an artery or vein. The system ordinarily includes a guidewire insertable within a guiding catheter, which has an occlusion balloon disposed about its distal end. The guidewire has an expandable filter, which can be collapsed to pass through a lumen and distal port of the guiding catheter. The lumen is adapted to receive a variety of endovascular devices, including angioplasty, atherectomy, and stenting catheters. Fluid medium or blood can be infused through the lumen of the guiding catheter to flush embolic material or mobile plaque generated during the endovascular procedures toward the expanded filter deployed downstream from the region of interest. Methods of using the filter flush system to entrap and remove embolic material from the vessel are also disclosed.

U.S. Pat. No. 6,786,896 to Madhani et al. discloses a method of performing surgery, comprising: using a remotely-controlled robotic surgical instrument having an elongate shaft with a longitudinal axis and a distal end, said distal end coupled to a wrist element. The wrist element fiber is coupled to an end effector, the wrist element has a plurality of wrist segments pivotally jointed together, tracks the motion of a moving portion of a patient's beating heart. The device has at least a portion of the wrist element to permit the end effector element to track motion of the moving heart portion without moving the longitudinal shaft of the instrument.

U.S. Pat. Nos. 6,926,670 and 6,968,743 disclose devices including an implantable microfabricated mechanism capable of being entirely implanted within a human body; the devices including biocompatible monolithic structure.

In U.S. Pat. No. 6,926,670, Rich et al. discloses an implantable microfabricated sensor device and method for measuring a physiologic parameter of concern within a human body. The implantable gadget is a micro electromechanical system (MEMS) device and includes a substrate having an integrated inductor and one sensor created.

Rich et al., U.S. Pat. No. 6,968,743 discloses a device that also relates to the field of micro-electromechanical systems (MEMS) sensors, in which a MEMS capacitive sensor is optimized for implantation into the body of a patient to enable measurement one or more physiologic parameters.

In U.S. Pat. No. 7,607,440, Coste-Maniere, et al. describes methods and a device for enhancing surgical planning to provide enhanced planning of entry port placement and/or robot position for laparoscopic, robotic, and other minimally invasive surgery. Various embodiments may be used in robotic surgery systems to identify advantageous entry ports for multiple robotic surgical tools into a patient to access a surgical site. Generally, data such as imaging data is processed and used to create a model of a surgical site, which can then be used to select advantageous entry port sites for two or more surgical tools based on multiple criteria. Advantageous robot positioning may also be determined, based on the entry port locations and other factors. Validation and simulation may then be provided to ensure feasibility of the selected port placements and/or robot positions. Such methods, apparatus, and systems may also be used in non-surgical contexts, such as for robotic port placement in munitions diffusion or hazardous waste handling.

U.S. Pat. No. 7,647,831, Corcoran et al. describes a method for measuring pressure inside an anatomical fluid system. The method ascertains fluid pressure inside a vessel without compromising the integrity of the vessel. A sensor is positioned in operative communication with the external wall of the vessel such that expansion of the external wall of the vessel exerts a force against the sensor that is directed substantially radially outward with respect to the vessel. A substantially radially inward force is caused to be directed against the sensor in response to the substantially radially outward force exerted by the external vessel wall. The sensor can thus be used to detect the magnitude of the substantially radially outward force. The apparatus includes a sensor and a band operatively associated with the sensor and configured to at least partially encircle the vessel so as to retain the sensor in operative communication against the external wall of the vessel.

Fonseca et al. in U.S. Pat. No. 7,699,059 discloses an implantable wireless sensor. The sensor is a wirelessly controlled, unpowered, micromechanical, flexible sensor that can be delivered using endovascular techniques, to measure a corporeal parameter such as pressure or temperature. A sensor is introduced into the body by the steps of folding or rolling the sensor into a cylinder, loading it into a catheter, and deploying into an aneurysm sac, then allowing it to unroll or unfold, either by itself or facilitated by the incorporation of a super-elastic alloy component.

Joy et al., U.S. Pat. No. 7,839,153 discloses an invention that communicates with a wireless sensor implanted within the human body to measure a physical condition. The invention determines the resonant frequency of a sensor by adjusting the phase and frequency of an energizing signal until the frequency of the energizing signal matches the resonant frequency of the sensor. The system energizes the sensor with a low duty cycle, gated burst of RF energy having a predetermined frequency or set of frequencies and predetermined amplitude. The energizing signal is coupled to the sensor via magnetic coupling and induces a current in the sensor, which oscillates at the resonant frequency of the sensor. The system uses a pair of phase locked loops to adjust the phase and the frequency of the energizing signal.

Prisco et al., U.S. Pat. No. 7,899,578 discloses an invention that relates to medical robotic systems. This type of invention indicates the improvements with respect to medical robotic systems such as those used in performing minimally invasive surgical procedures. It is now becoming more common that robotic procedures offer many benefits over traditional open surgery techniques. Because of robotic surgical procedures, the advantages of: less pain, shorter hospital stays, quicker return to normal activities, minimal scarring, reduced recovery time, and less injury to tissue. Consequently, demand for minimally invasive surgery using such medical robotic systems is strong and growing.

Lamprecht et al., U.S. Pat. No. 7,907,166, discloses a robotic surgical system comprising: a master control console having a stereo viewer to view stereo images of a surgical site; a surgical manipulator coupled to the master control console to receive control signals, the surgical manipulator including a first robotic arm and a second robotic arm, a surgical instrument coupled to the first robotic arm, and a stereo endoscopic camera coupled to the second robotic arm, the stereo endoscopic camera responsive to the control signals to generate stereo video images of the surgical site; a stereo telestration system coupled between the stereo endoscopic camera and the stereo viewer; and a telestration generator coupled to the stereo telestration system. The telestration generator generates telestration graphics for overlay on the stereo images of the surgical site; wherein the stereo telestration system is configured to generate left and right images of the telestration graphics by effectively positioning the telestration graphics at a desired depth relative to the stereo images of the surgical site by adjusting a disparity between the left and right images of the telestration graphics and combine the left and right images of the telestration graphics with corresponding left images and right images of the stereo images of the surgical site for stereo viewing of the telestration graphics with the stereo images of the surgical site in the stereo viewer.

Allen et al. in U.S. Patent Application Publication No. US 2007/0210786 discloses an invention that determines the resonant frequency of a sensor by adjusting the phase and frequency of an energizing signal until the frequency of the energizing signal matches the resonant frequency of the sensor. The system energizes the sensor with a low duty cycle, gated burst of RF energy having a predetermined frequency or set of frequencies and predetermined amplitude. The energizing signal is coupled to the sensor via magnetic coupling and induces a current in the sensor, which oscillates at the resonant frequency of the sensor. The system receives the ring down response of the sensor via magnetic coupling and determines the resonant frequency of the sensor, which is used to calculate the measured physical parameter. The system uses a pair of phase locked loops to adjust the phase and the frequency of the energizing signal.

Hasser et al. in U.S. Patent Application Publication No. US 2007/0167702 discloses a medical robotic system that provides 3D telestration over a 3D view of an anatomical structure by receiving a 2D telestration graphic input associated with one of a pair of stereoscopic images.

Many deaths have been reported due to blockage of human vessels, accordingly, there is a need in the art for less invasive repair procedures for repairing patient vessel obstruction and other defects in arteries such as the aorta or other arteries or vessels.

There is a continuing need for improvement with respect to methods, systems and devices for executing angioplasty procedures, preferably improvement that do not require major surgery, or continued use of drugs and which may be used on higher risk patients than what conventional angioplasty surgery currently allows.

SUMMARY OF THE INVENTION

In one aspect of the present invention, a clearing module is provided that includes: a main body configured and dimensioned to be received within a vessel or duct of a patient, adjacent a surgical target area in the patient, the main body including: an instruction receiving unit configured to receive wireless instructions from an instruction transmitter located outside the patient's body while the module is located inside of the patient's body; a positioning element configured to be monitored by a system external of the patient's body while the positioning element is inside the patient's body; and a destructive energy emitter configured to emit destructive energy from the module toward the surgical target area according to instructions received from the instructions receiving unit.

In at least one embodiment, the module further includes a non-destructive energy receiving unit configured to receive non-destructive energy from an energy transmitting unit located outside of the patient's body, while the non-destructive energy receiving unit is located inside of the patient's body.

In at least one embodiment, the module is further configured to convert the non-destructive energy to destructive energy.

In at least one embodiment, the module further includes an energy conversion unit configured to receive the non-destructive energy from the non-destructive energy receiving unit and further configured to convert the non-destructive energy to another modality of energy.

In at least one embodiment, the module further includes a destructive energy transmission unit configured to receive the another modality of energy and convert the another modality of energy into destructive energy.

In at least one embodiment, the module further includes a destructive energy emitter configured to receive the destructive energy from the destructive energy transmission unit and emit the destructive energy from the module toward the surgical target area.

In at least one embodiment, the module further includes a guide bar and communication interface configured to transfer instructions from the instruction receiving unit to other locations in the main body.

In another aspect of the present invention, a system for treating a patient is provided that includes: a control subsystem located externally of the body of the patient, the control subsystem including a non-destructive energy transmitter; and a clearing module configured and dimensioned to be received within a vessel or duct of the body of the patient; the clearing module including: a positioning element configured to be monitored by the sub-system external of the patient's body while the positioning element is inside the patient's body; and a non-destructive energy receiving unit configured to receive non-destructive energy from the non-destructive energy transmitted located outside of the patient's body while the non-destructive energy receiving unit is located inside of the patient's body; and wherein the control subsystem is configured to drive and guide the clearing module along a pathway inside of the patient to a predetermined location adjacent a surgical target.

In at least one embodiment, the control subsystem includes a nuclear magnetic resonance (NMR) machine configured to drive and guide the clearing module along the pathway inside of the patient to the predetermined location adjacent the surgical target.

In at least one embodiment, the clearing module is configured to convert the non-destructive energy received by the non-destructive energy receiving unit to destructive energy.

In at least one embodiment, the clearing module is configured to emit the destructive energy from the module toward the surgical target.

In at least one embodiment, the control subsystem includes a wireless instruction transmitter and the module includes an instruction receiving unit configured to receive wireless instructions from the wireless instruction transmitter located outside the patient's body while the module is located inside of the patient's body.

In at least one embodiment, the control subsystem includes a wireless instruction transmitter and the module includes an instruction receiving unit configured to receive wireless instructions from the wireless instruction transmitter located outside the patient's body while the module is located inside of the patient's body; and wherein instructions received by the instruction receiving unit include instructions for controlling the conversion of non-destructive energy to destructive energy.

In at least one embodiment, the control subsystem includes a wireless instruction transmitter and the module includes an instruction receiving unit configured to receive wireless instructions from the wireless instruction transmitter located outside the patient's body while the module is located inside of the patient's body; and wherein instructions received by the instruction receiving unit include instructions for emitting the destructive energy and for controlling at least one characteristic of the destructive energy that is emitted.

In another aspect of the present invention, a method of treating a patient is provided that includes: introducing a module into a vessel or duct of the patient; driving the module through the vessel or duct and to a location adjacent a predetermined surgical target, wherein the driving is performed by applying a force from outside of the patient to the module located inside the patient; wirelessly receiving instructions at the module, from an instructions transmitted outside the body of the patient; and emitting destructive energy from the module toward the surgical target, in accordance with the instructions received.

In at least one embodiment, the force applied from outside the body of the patient is a magnetic force.

In at least one embodiment, the destructive energy comprises laser energy.

In at least one embodiment, the method further includes receiving non-destructive energy at the module, wirelessly from a non-destructive energy transmitter located outside of the patient while the module is located inside of the patient.

In at least one embodiment, the method further includes converting the non-destructive energy received to the destructive energy.

In at least one embodiment, the non-destructive energy comprises X-ray energy.

These and other features of the invention will become apparent to those persons skilled in the art upon reading the details of the modules, systems and methods as more fully described below.

DETAILED DESCRIPTION OF THE INVENTION

Figure 1:
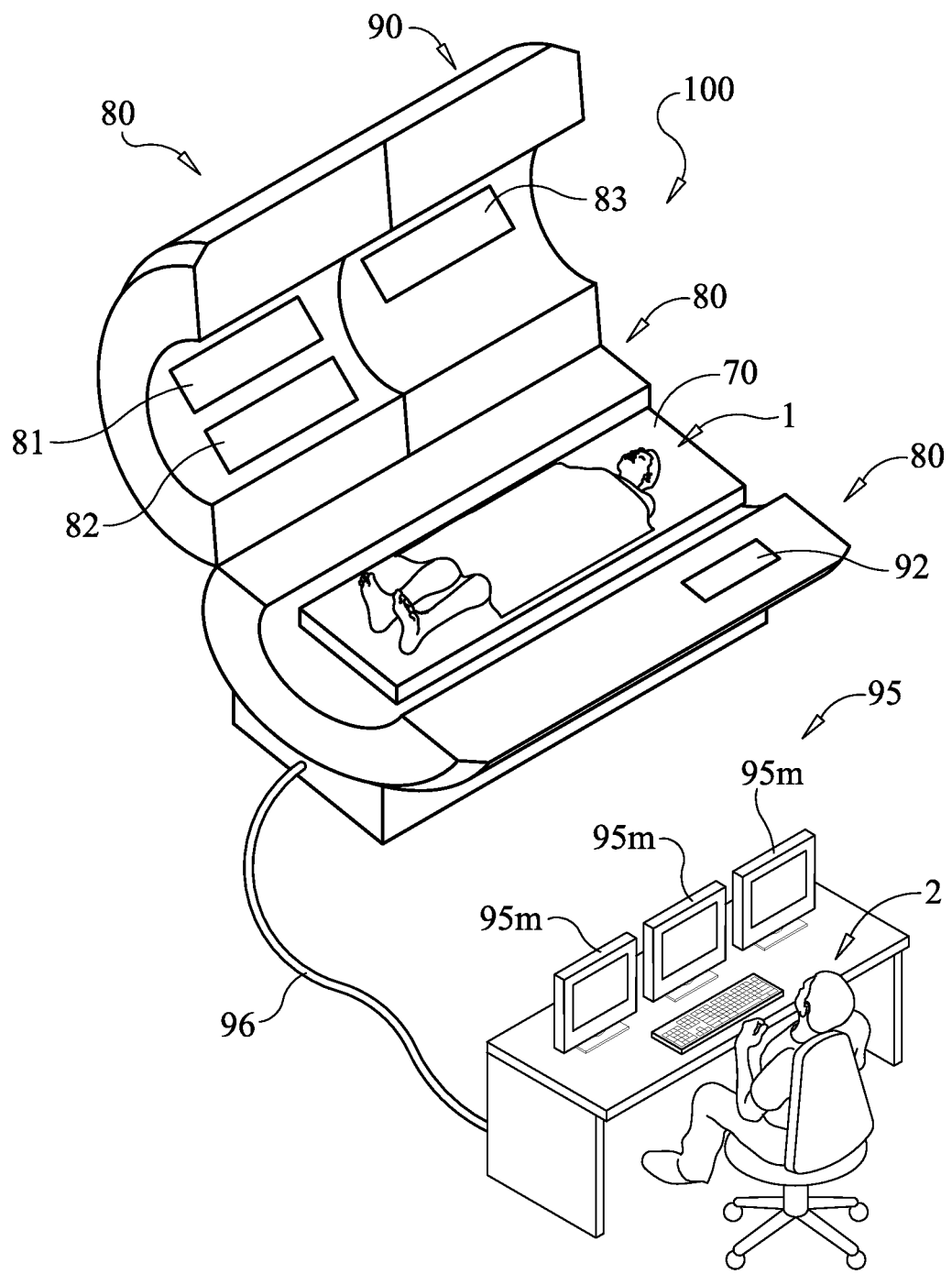
FIG. 1 schematically illustrates an automated vessel clearing system according to an embodiment of the present invention.

Before the present systems, devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a beam transmission unit" includes a plurality of such beam transmission units and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "patient" herein refers to a human patient who may be an adult or child, male or female. Further, the term patient, as used herein, includes mammalian species of all types, genders and developmental stages.

"Nanotechnology" generally refers to technology relating to structures sized between about 1 to about 100 nanometers in at least one dimension, and involves developing materials or devices within that size. Quantum mechanical effects are very important at this scale. Nanotechnology is very diverse, fluctuating from enlargement of conventional device physics to completely new approaches based upon molecular self-assembly, from flourishing new materials with dimensions on the nanoscale to exploring whether one can directly control matter on the atomic scale. Nanotechnology may be able to create many new materials and devices with a vast range of applications, such as in medicine, electronics, biomaterials and energy production.

"Micro-Electro-Mechanical Systems" (MEMS), involves the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices. Microelectromechanical systems (MEMS) (also written as micro-electro-mechanical, Micro-ElectroMechanical or microelectronic and microelectromechanical systems) is the technology of very small mechanical devices driven by electricity; it merges at the nano-scale into nanoelectromechanical systems (NEMS) and nanotechnology. MEMS are made up of components between 1 to 100 micrometers in size (i.e. 0.001 to 0.1 mm) and MEMS devices generally range in size from 20 micrometers (20 millionths of a meter) to a millimeter. They usually include a central unit that processes data, the microprocessor and several components that interact with the outside such as microsensors. The following materials have been used to construct MEMS devices, single crystal silicon (Si), polycrystalline silicon (polysilicon), silicon oxide (SiO2), silicon nitride (Si3N4), single crystal cubic silicon carbide (3C-SiC or b-SiC), titanium (Ti).

An "integrated circuit" (IC) or is an electronic circuit manufactured by the patterned diffusion of trace elements into the surface of a thin substrate of semiconductor material. Integrated circuits (IC) are constructed of semiconducting materials, which are midway between good conductors, like copper, and insulators such as plastic. Silicon is the current favorite. Ultrapure silicon is mixed with small, precise amounts of other elements to create electronic materials with different characteristics. Additional materials are deposited and patterned to form interconnections between semiconductor devices. The integrated circuit (IC) is one of the most complex things ever made. Integrated circuits may be small squares of silicon, imprinted with microscopic patterns. The patterns may contain hundreds of millions of transistors, resistors and other electronic parts.

"Nuclear Magnetic Resonance" (NMR) was described independently by Felix Bloch and Edward Mills Purcell in 1946 both of whom shared the Nobel Prize in physics in 1952 for their discovery. The development of NMR as a technique of analytical chemistry and biochemistry parallels the development of electromagnetic technology. This technique allows the detection of radio frequency energy, and on the absorption of such energy by matter.

"Computerized Axial Topography (CAT)/CT (computed tomography), sometimes called CAT scan, uses special x-ray equipment to obtain image data from different angles around the body and then uses computer processing of the information to show a cross-section of body tissues and organs.

Recent technical advances with respect to CT scanners now enable 192 images of the body per second. This non-invasive, virtually pain-free procedure offers exceptional image quality, which can mean better diagnosis, faster recovery time and increased patient comfort and convenience.

"Internet Protocol Packet" (IP Packet) is the smallest message entity exchanged via the Internet Protocol across an Internet Protocol version 6 (IPv6) network. Packets consist of control information for addressing and routing, and a payload consisting of user data. The control information in IPv6 packets is subdivided into a mandatory fixed header and optional extension headers. The payload of an IPv6 packet is typically a datagram or segment of the higher-level Transport Layer protocol, but may be data for an Internet Layer (e.g., ICMPv6) or Link Layer (e.g., OSPF) instead.

"Magnetic Resonance Imaging" (MRI) is a unique imaging method because, unlike the usual radiographs (x-rays), radioisotope studies or even Computed Tomography (CT) scanning, it does not rely on ionizing radiation. Instead radio frequency waves are directed at protons, the nuclei of hydrogen atoms, in a strong magnetic field. The protons are first "excited" and then "relaxed," emitting radio signals that can be computer-processed to form an image. In the body, protons are most abundant in the hydrogen atoms of water—the "H" of $H_2O$—so that an MR image shows differences in the water content and distribution in various body tissues.

"Nuclear Scans": in some instances, a doctor may request that someone have a nuclear scan. A nuclear scan involves only a small "tracer" dose of radioactive material, and is not dangerous. Once this tracer element is injected into a patient's system, it can be followed through the system as the patient lies directly underneath a sensing device. A nuclear scan is most often used to assess body function. Other uses include measurement of stomach emptying and localization of intestinal bleeding. Nuclear scans require very little preparation.

A "laser" device is a device that emits light (electromagnetic radiation) through a process of optical amplification based on the stimulated emission of photons. The term "laser" originated as an acronym for Light Amplification by Stimulated Emission of Radiation. The emitted laser light is notable for its high degree of spatial and temporal coherence, unattainable using other technologies. Spatial coherence typically is expressed through the output being a narrow beam which is diffraction-limited, often a so-called "pencil beam." Laser beams can be focused to very tiny spots, achieving a very high irradiance. Or they can be launched into a beam of very low divergence in order to concentrate their power at a large distance.

"X-radiation" (composed of X-rays) is a form of electromagnetic radiation. X-rays have a wavelength in the range of 0.01 to 10 nanometers, corresponding to frequencies in the range 30 petahertz to 30 exahertz ($3\times10^{16}$ Hz to $3\times10^{19}$ Hz) and energies in the range 120 eV to 120 keV. They are shorter in wavelength than UV rays and longer than gamma rays. In many languages, X-radiation is called Röntgen radiation, after Wilhelm Conrad Röntgen, who is usually credited as its discoverer, and who had named it X-radiation to signify an unknown type of radiation. Recently uncovered archival evidence shows that the original discoverer of X-rays was a Ukrainian physicist Ivan Pulyui, who worked in Vienna together with Röntgen and shared the results of his work with him. Correct spelling of X-ray(s) in the English language includes the variants x-ray(s) and X ray(s). XRAY is used as the phonetic pronunciation for the letter x. X-radiation used in the present invention is "non-destructive X-radiation" (X-ray energy) that doesn't significantly destroy or damage human tissue, such as the X-ray energy typically used for performing chest X-ray imaging, dental imaging, fluoroscopy and the like.

"Destructive energy" as used herein, refers to energy, such as laser energy, RF energy, microwave, cryogenic, ultrasound or other mode of energy applied at wavelength, power and/or time configured to damage or destroy human tissue, for example for ablating an obstruction within a vessel, ablation of a tumor, etc. Destructive energy is applied to damage, vaporize or destroy patient tissue.

"Beam transmission /clearing energy", as used herein, refers to destructive energy used to destroy, ablate, vaporize or otherwise remove tissue. This is distinguished from non-destructive energy such as X-rays (as used herein) and wireless communication signals, for example.

"Guide, control instructions RF energy", as used herein, refers to wireless RF signals used to control a module as described herein. For example, wireless RF instructions can be sent from a master NMR machine instruction transmitter to an instruction receiving unit of a module.

Two broad types of energy are referred to: destructive energy (examples of which include, but are not limited to beam transmission/clearing energy) and nondestructive energy (examples of which include, but are not limited to control instructions).

Detailed Description

The present invention provides embodiments that overcome shortcomings of the prior art by using one or more advanced technologies, including semiconductor-manufacturing methodology, nano-manufacturing techniques to produce an internal vessel-clearing module. After inserting the module into a patient's body, the invention allows the detection of the vessel clearing module, and controlling, positioning and guiding the module to clear a vessel or duct by means of a Nuclear Magnetic Resonance (NMR) control system. Accordingly, a systems that provides for the detection, control and positioning of a module within the vessel or duct in need of clearing is provided.

The present invention relates to the medical forecasting of arterial diseases or obstructions, and particularly to detection of vulnerable material within the vessel system. The invention provides methods of detection of obstructive accumulations within the arterial or other vessel systems, as wells a ducts within the human body and the elimination of these obstructions.

Various embodiments of the present invention include one or more of manufacturing of the device (module), the detection of the module, guiding and controlling, positioning and using the module to clear the vessel by means of a Nuclear Magnetic Resonance (NMR) control system. Within the scope of at least one embodiment of the present invention, a module is produced, allowing for computer-assisted surgery of the procedure within the vessel to be cleared of the obstruction. The vessel-clearing module will be controlled and guided by a method described by Zurn in U.S. Patent Application Publication No. US 2009/0062639 A1, filed on Aug. 27, 2007, which is hereby incorporated herein, in its entirety, by reference thereto.

A module such as described according to an embodiment of the present invention can be used in many medical applications. As mentioned, it may be employed in miscellaneous types of vessel clearing of vessels. The invention can be used to sustain and keep open vessels of venous systems, to close pathological vessel deficiency, etc.

According to an embodiment of the present invention, a biocompatible MEMS module, is assembled, including: a communication element configured to receive radio frequency energy from a source external of the device; radio frequency receiving unit; a communication link between the communication element and each of the MEMS device regions.

According to an embodiment of the present invention, a module may be constructed using nano technology to create a microelectromechanical device (MEMS). Each module may have different dimensions, such as dimensions of (100×100×50 microns): smaller modules will be necessary for smaller vessel clearing, such as: capillaries in the brain. The size of the module is determined, at least in part, by the inside diameter of the vessel in need of clearing.

Figure 2A:
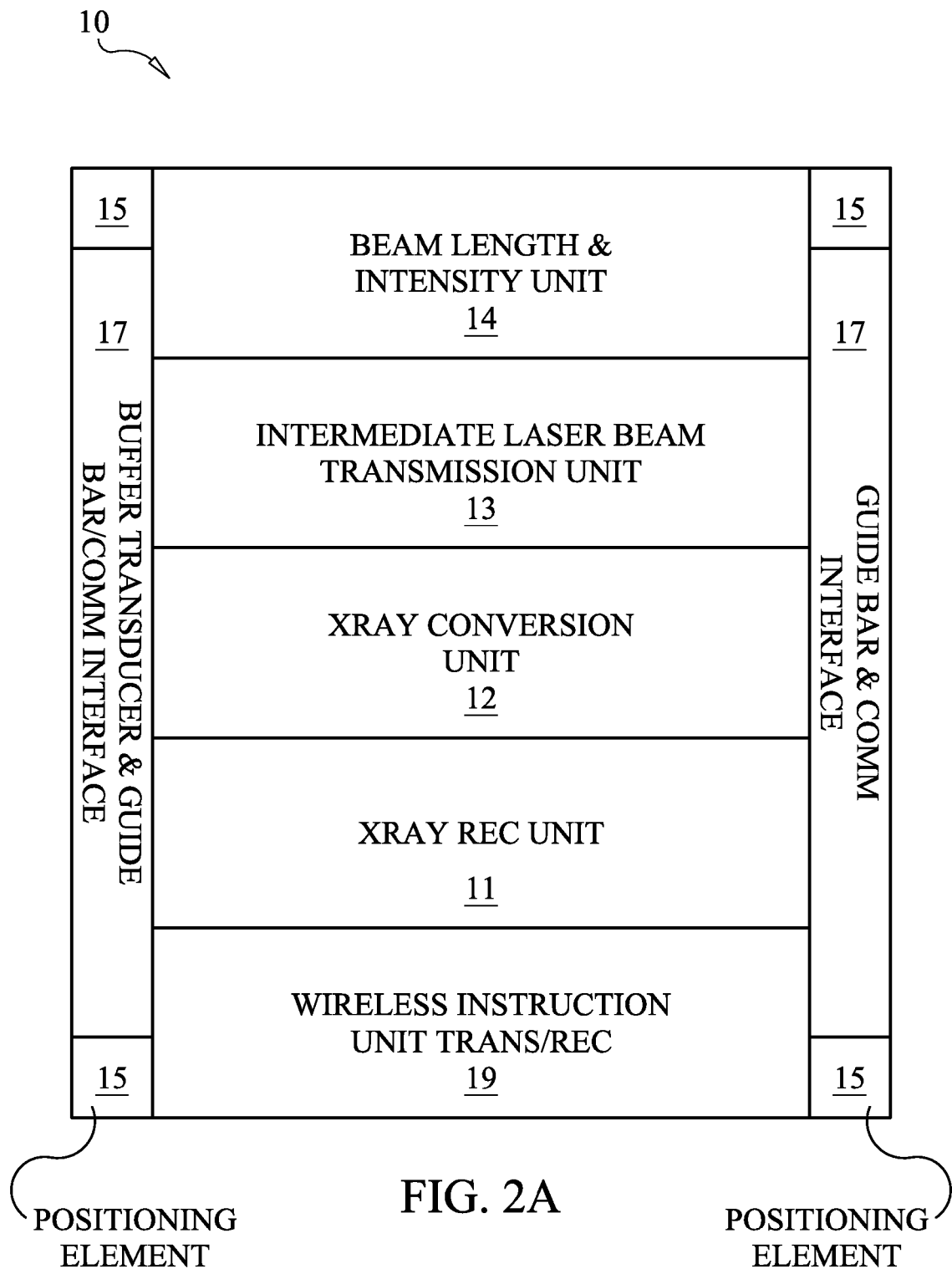
FIG. 2A is a schematic illustration of a biocompatible clearing module according to an embodiment of the present invention.
Figure 2B:
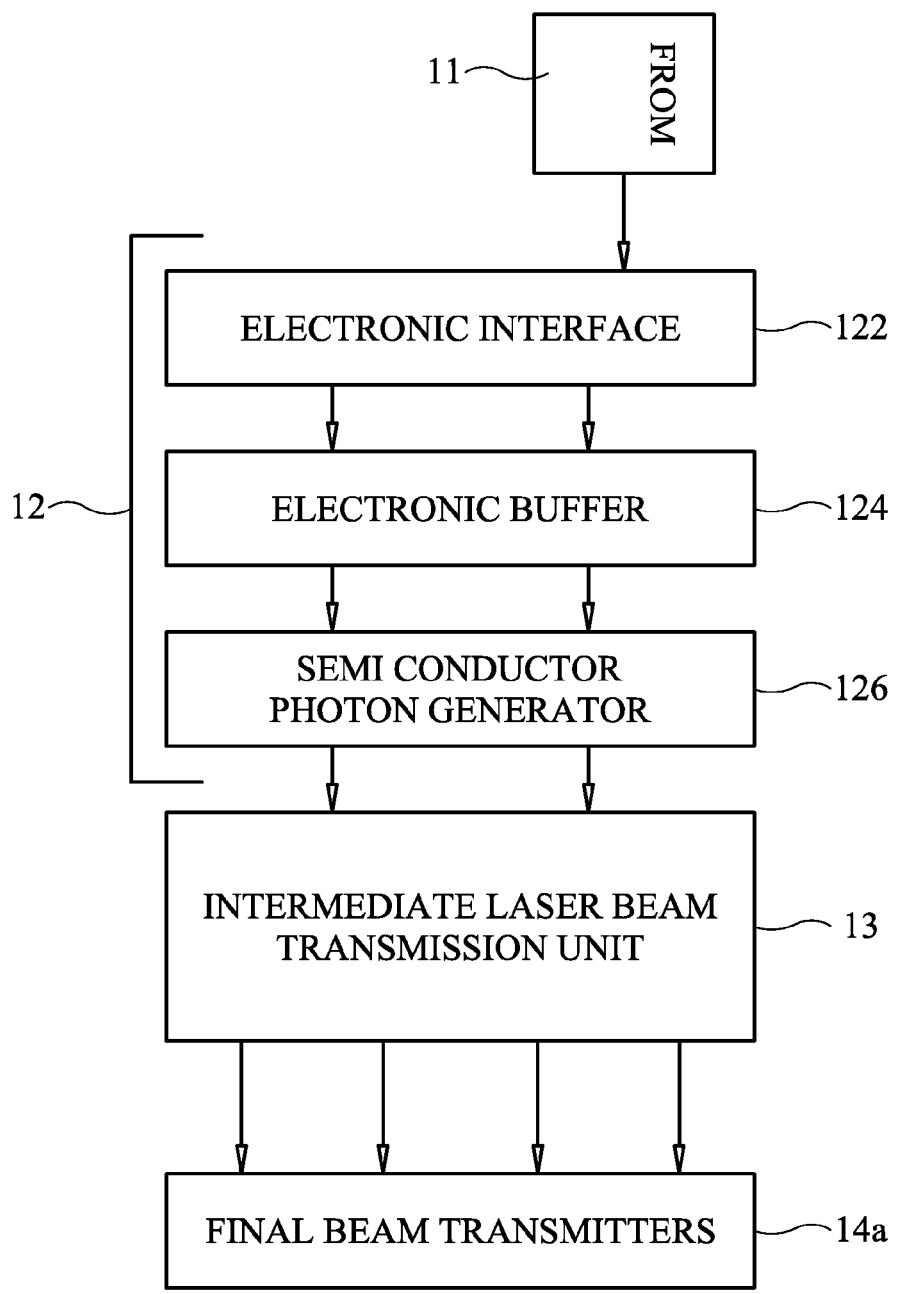
FIG. 2B is an expanded block diagram indicating an electronic interface, electronic buffer and semiconductor photon generator indicating additional circuits within an x-ray energy conversion section, according to an embodiment of the present invention.

According to at least one embodiment, a vessel clearing module includes the following sections: wireless instructions transmit/receive unit 19, X-ray receiving unit 11, X-ray energy conversion unit 12 (which includes additional circuits illustrated in FIG. 2B). Also included in the module, according to at least one embodiment, are an intermediate laser beam transmission unit 13, multiple final beam transmitter units 14a in beam length & intensity unit 14 and guide and transducer bar 17. Guide and transducer bar includes communication circuits (bus) connecting to all sections within the module 10. Further included within the module 10, according to at least one embodiment of the present invention, are positioning elements 15. Transmit/receiving unit 19 also transmits real time information from module 10 to the master machine 100.

According to at least one embodiment, two types of energy are sent to module 10 from master machine 100: wireless instruction signals are sent to section 19 to guide and control the movement of the module 10, and X-ray energy is sent to section 11 which is converted into destructive laser energy in the module 10. The wireless instructions are received by the wireless instruction transmit/receiving unit 19 and are then transmittable via the communication links (paths) within 17 to other module sub-sections within the module 10. The guide and control wireless instructions are in the form of information packets. The X-ray energy is converted to laser beams to remove the blockage.

According to at least one embodiment, module 10 receives two types of non-destructive energy: X-ray and wireless instructions (e.g., in the form of RF energy). The X-ray energy is converted to destructive energy in the form of laser energy. The wireless instructions are used for guiding and controlling module 10 according to an embodiment of the present invention. The non-destructive energy is supplied to the module from a source outside of the patient's body, e.g., from a NMR machine or other controller. The X-rays are within a voltage range of from about 12 to about 120 keV (0.10 to 0.01 nm wavelength), and are applied in short duration not harmful to the human body. The wireless instructions are provided as RF energy conforming to IEE 802.11 standards used in implementing wireless local area network (WLAN) computer communications in the 2.4, 3.6 and 5 GHz frequency bands.

According to at least one embodiment, X-ray energy, received by the X-ray receiving unit 11, is converted to laser energy by the X-ray conversion unit 12 and used to deliver a laser beam as the beam transmission/clearing energy (destructive energy) that will be used in the beam transmission section, described below, to destroy tissue, such as when cleaning/clearing a vessel/duct. The intermediate beam transmission section 13 transmits laser energy in the form of a laser beam, through the final beam transmitters 14a (e.g., see FIG. 3), targeted to tissue to be destroyed. The intermediate laser beam transmission unit 13 transmits the laser beam energy to the multiple final laser beam transmitters 14a in section 14.

Coded wireless instructions (guide & control signals) may be sent to the module 10 to guide and control it. The instructions are sent from an instruction transmit/receiving unit 83 outside the patient's body to an instruction transmit/receiving unit 19 of the module inside the patient's body. Instructions are sent within a packet string in either direction. The method of delivery of the instructions is similar to the Internet Protocol packet. The packet contains header, body and trailer information that is decoded by the MEMS module for controlling functions of the module. The instructions are sent from a down link transmission unit (within the NMR section), received, then decoded within the clearing module and processed. The instructions are executed by the module to guide and control the module to perform the necessary procedures.

In at least one embodiment, data transmission from a MEMS clearing module, referred to as an uplink transmission, transmits to a master NMR information which is necessary for fine tuning adjustments with respect to the sensors, guide circuitry and beam transmission. This allows for "real time" feedback to control the motion and beam transmission within the MEMS module. Data transmission from the NMR, referred to as a downlink transmission, transmit information to the MEMS clearing module necessary for controlling the sensors within the beam transmission section and guide circuitry. This data from the NMR may adjust sensing activities, guide activities, and beam transmission of the MEMS module as alternating conditions occur.

Wireless instruction signals, used to guide and control the module, are transmitted to section 19 and X-rays are transmitted to section 11 which are converted into laser beam destructive energy to clear the blockage. Wireless instructions are sent in a structured method (packet steam), whereas X-rays are transmitted and converted to beam transmission energy.

In at least one embodiment, a beam transmitting sub-section contains four transmit elements, each with its own independent intensity and beam length controls. The beam transmitting subsections comprise MEMS tunable (adjustable) lasers, each with a variable wavelength adjustable beam. The control signals for operating the beams transmitting subsections are wireless instructions received by section 19 from the master machine 100 outside of the patient.

Nuclear Magnetic Resonance (NMR) techniques are used for positioning and guiding the module(s) according to an embodiment of the present invention during a procedure on a patient. Precise movement of the module is critical to avoid damaging a vessel wall or any other human tissue that is not intended to be destroyed or removed during the procedure.

Modules according to the present invention are made of material tolerated by the human body, and can be applied within blood vessels and/or ducts in the body of a living animal, a living human or some other intricate accessible place within either. Modules can comprise a resilient flexible substance substantially inert to bodily fluids (e.g., silicone, or other biocompatible polymer having similar properties).

In at least one embodiment, a buffer transducer and guide sub-section of the module contains MEMS sensors that control the module in relationship to contact with the vessel wall tissue and the obstructive material in the area of the vessel to be cleared. The sensors also permit differentiating between different levels of rigidity in vessel wall tissues and blocking material tissues. The sensors contain ultrasound transducers that are configured to differentiate between vessel wall tissue and obstructive tissue, see also U.S. Pat. No. 7,967,754 and Guest Editorial, "Fantastic voyage through the cardiovascular system", Eur J. Echocardiography (2004) 5, 8-11, both of which are hereby incorporated herein, in their entireties, by reference thereto.

Integration of transducers, sensors, actuators, and other microstructures within the electronics of a module, according to an embodiment of the present invention, provides the ability to transform medicine and surgery from surgery by skilled doctors, to computer assisted surgery by skilled technicians or engineering personnel.

Methods of positioning modules are provided, using a Nuclear Magnetic Resonance (NMR) control system to monitor the positioning of the modules. In at least one embodiment, positioning and guiding of a module is facilitated by provision of a small "tracer" dose of radioactive material that is not hazardous to the patient that it is inserted into. Once the module with the tracer element is injected into the vessel or duct, the NMR system can directly track the location of the module at all times.

Sensitive features of the module measure: quantities of pressure, hardness of the vessel wall, blood flow within the vessel. The ultrasound transducers within the buffer transducer and guide bar are configured for use to differentiate between the vessel wall and the blockage/obstructive material. The transducers are also configured for use in sensing blood pressure and blood flow within the vessel. These sensing features allow real time feedback, for use in guiding and positioning the module, as well as directing destructive energy to the obstructive material, but not at the vessel wall or any other tissue that is not intended to be destroyed. The real time feedback allows the constant adjustment of beam length and intensity from the beam transmitting sub-section that is clearing the vessel of the blocking material. Tunable lasers used can be adjusted as to the wavelength of light emitted. In at least one embodiment, the wavelength is 1310 nm, with a range of 110 nm, i.e., a range of from about 1255 nm to about 1365 nm preferred, although the present invention is not limited to this range. In at least one embodiment, MEMS sensors differentiate between the material blocking the vessel and the vessel walls, facilitating real time control and guidance of the module.

As changes in the material to be cleared or changes in the characteristics of the vessel wall change, adjustments to the movement of the module may be made (e.g., speed up or slow down): also to the beam length and intensity to allow for sensing changes in the blocking material and vessel walls.

Modules, methods and systems described herein may alternatively be used to clear urinary tracts of blockage, as well as to treat other difficult to approach places within the patient's body. For example, modules according to embodiment of the present invention may be used to treat other structures in, but not limited to the respiratory, biliary, or urinary tracts to clear blockages.

Methods described herein are rapid and thus avoid substantial blocking of the flow of blood through the vessels, since the module is rapidly delivered, operated and removed from the body.

In at least one embodiment a method of treatment ascertains fluid pressure inside a vessel without compromising the integrity of the vessel.

Turning now to FIG. 1, an automated vessel clearing system 100 is schematically shown. A patient 1 is positioned on a table 70, with elements of an NMR (nuclear magnetic resonance) machine 80 below and above him/her. The patient 1 is almost fully enclosed by the CT/MRI (computerized tomography/magnetic resonance imaging) equipment 90 and NMR 80 machines. The top of the system 100 has a clamshell arrangement/configuration with the forward portion 90 containing CT/MRI equipment, which, in combination with NMR equipment 80 in the lower portion of system 100 is configured to perform nuclear magnetic resonance functions. Both CT/MRI and NMR machinery are currently available as known to those of ordinary skill in the art. The upper clamshell is configured to more back and forth (forwardly and rearwardly) over the patient 1 in directions toward the head (forward) and the feet (rearward) of the patient 1, so that either portion 80 or 90 can be located over any desired location of the patient 1. These elements of the system 100 allow control of the artery clearing module 10 (schematically illustrated in FIG. 2) during guiding and control thereof and provide RF energy and communication information and transmit the same to the artery clearing modules 10.

Also illustrated are the control panel 95 and operator 2 of the artery clearing system 100. In this example, the operator 2 is sitting at the system console/control panel 95 monitoring the artery clearing module's 10 movement into the patient 1. The system 100 includes CT/MRI equipment 90, NMR machine 80, X-Ray generating module 81, X-ray transmitting module 82, instructions transmitting module 83 and map processor 92. Control panel 95 is wired into the system 100 in the embodiment of FIG. 1, but could alternatively connect wirelessly. System/master machine 100 (including control panel 95) is configured to guide and move the vessel clearing modules 10. Control and communication signals are sent to the modules 10 within the patient 1 from instructions transmitting module 83. The system 100 is capable of guiding and controlling multiple modules 10 at the same time.

FIG. 2A is a schematic illustration of a biocompatible clearing module 10 according to an embodiment of the present invention. In at least one embodiment, module 10 comprises a MEMS device. Module 10 is fabricated using a combination of MEMS technology and integrated circuit technology. Module 10 includes multiple sub-sections/units. The X-ray receiving sub-section/unit 11 receives non-destructive X-ray energy from the X-ray transmitting module 82, which transmits the X-ray energy emitted by X-ray generation unit 81. Transmitting module 82 is focused on the module 10 and then emits the X-rays in a focused delivery to module 10, where they are received by receiving unit 11.

X-ray energy conversion unit 12 converts the X-rays received by X-ray receiving unit 11 to laser energy. As indicated in FIG. 2B, the X-rays from receiving unit 11 are sent through the electronic interface 122 of X-ray energy conversion unit 12 through electronic buffer 124 and to semiconductor photogenerator 126 which generates photons therefrom. X-ray energy conversion unit 12 then outputs the photons to intermediate laser beam transmission unit 13. The X-rays must be converted to an electronic signal by the electronic interface 122 that is buffered through buffer 124 and sent as an input to the photon generator 126. The X-ray energy conversion unit 12 converts the non-destructive X-ray energy received by X-ray energy receiving unit 11 to energy that is transmitted by use of the intermediate beam transmission unit 13. As shown in FIG. 2B, the X-ray energy conversion unit 12 includes an electronic interface 122 that converts the frequency of the X-rays received from X-ray receiving unit 11, and inputs an electronic signal to the semiconductor photon generator 126, where the electronic signal is converted to photons. An electronic buffer 124 may be provided between electronic interface 122 and photon generator 126, as illustrated in FIG. 2B, to buffer the energy flow from 122 to 126.

The intermediate laser beam transmission unit 13 prepares the photons received, splits the single channel of photons into multiple channels of photons (e.g., four channels in this example, although this number may vary) and transfers this destructive energy to the final beam transmitters 14a in beam length and intensity unit 14. The photons within unit 13 are split by the circuitry within the intermediate laser beam transmission unit 13 and then fed to unit 14. The final beam transmitters 14 in beam length and intensity unit 14 emit focused laser beams resulting from the commutation of the circuits between the electronic interface 122 and the final beam transmitters 14a, the circuits of which condition the laser beam outputs. The circuits between 122 and 14a condition the beams by means of on/off switches that allow bursts, variations in the electronic inputs to the circuits between 122 and the final beams transmitters' outputs that control the intensity of the beams and length of the beams. The intermediate 13 and final 14a beam transmitters also act as coarse and fine adjustments to the laser beams outputted. The beam length and intensity unit 14 contains multiple elements 14a which are the final beam transmitters (four elements 15 in the embodiment of FIG. 3, although more or fewer can be employed, even just one, although if only one is employed, then there is no need to split the photon in unit 13). Each element 14a is individually controllable to vary wavelength of the destructive energy emitted therefrom in a manner described above. Each element 14a is also individually controllable as to time of emission, burst length, amount of emission, etc. Each element 14a is also individually controllable as to orientation, such that the direction of aim of emission of the laser beam from each can be individually controlled, thereby providing localized beam control.

A buffer/transducer/guide bar/communication bar 17 is provided on two opposite sides of module 10 as illustrated in FIG. 2A. Redundancy is provided by providing a pair of bars 17 to ensure optimum functioning whether either the right side or left side of the module 10 is in contact with a vessel wall. Instruction receiving unit 19 receives control signals in the form of wireless RF signals, from the instruction transmission module 83 of CT/MRI section 90. The instruction transmission module 83 is a subsection of the top clam shell 90. The top clam shell contains X-ray generation module 81, X-ray transmission module 82 and instruction transmission module 83. Instruction transmission module 83 sends instructions to guide and control the module 10. Instruction receiving unit 19 receives the instructions from module 83 and transfers the instructions to the various units (11, 12, 13, 14, 15 and 17) of module 10. Thus, instruction receiving unit 19 has multiple functions, in that it not only sends guide and control instructions to Guide Bar and Communications Interface bars 17, but it also sends instructions to control the activities within the sub-sections of the module (11, 12, 13, 14, 15). The communication link within the buffer/transducer of the guide bar and communication interface 17 is a computer bus structure that links all of the units (11,12,13,14,15) in communication with the instruction receiving unit 19. The X-ray transmitting module 82 sends X-ray energy (non-destructive) to X-ray receiving unit 11 and the instructions transmission module 83 send wireless instructions energy (non-destructive) to instruction receiving unit 19.

Figure 3:
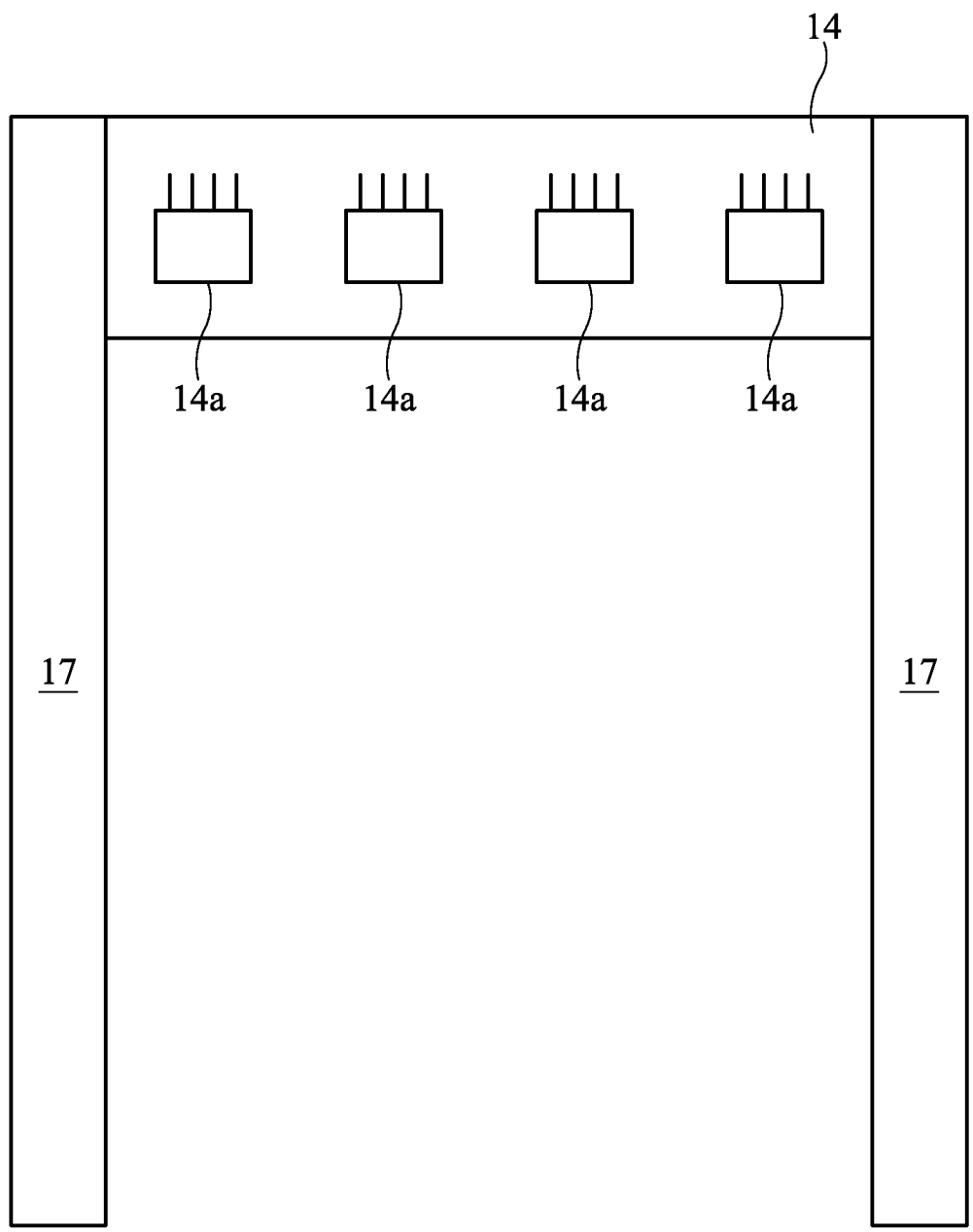
FIG. 3 schematically illustrates a partial view of a biocompatible clearing module having four final beam transmission elements within a final beam transmitter according to an embodiment of the present invention.

FIG. 3 schematically illustrates a partial view of a biocompatible clearing module 10 having four beam transmission elements 14a within a final beam length and intensity unit 14 according to an embodiment of the present invention. The final beam transmission elements 14a include tunable lasers, the outputs of which are controlled by adjustable inputs received via guide gar and communication interface 17 from instructions receiving unit 19.

Figure 4:
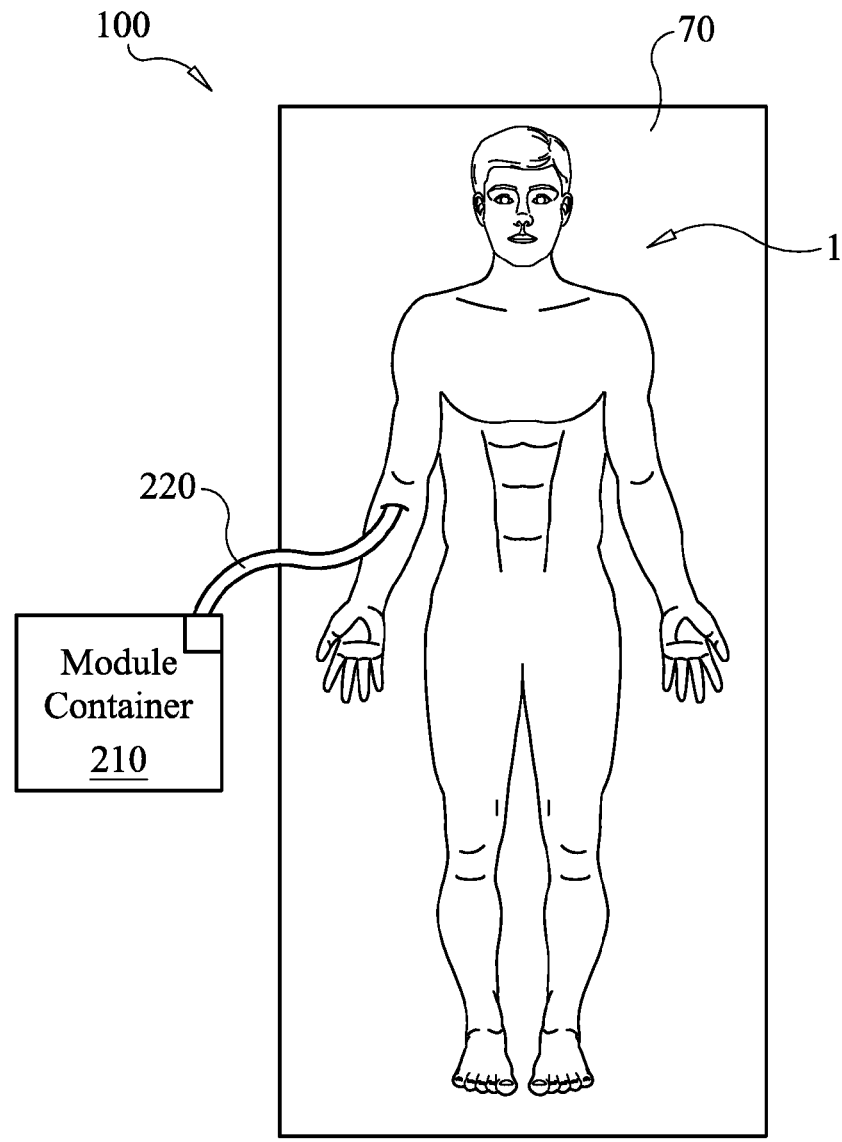
FIG. 4 schematically illustrates a patient inside a main machine of the system during treatment, according to an embodiment of the present invention.

FIG. 4 schematically illustrates a patient 1, inside the main machine of the system 100 during treatment, according to an embodiment of the present invention. A clearing module container 210, accommodates the pre-manufactured vessel clearing modules 10 prepared for use within the system 100. Multiple modules 10 of different sizes may be used, depending upon the requirements of the procedure. Also shown in FIG. 4, is the connection tube 220, to intravenously or intra-arterially transfer the module 10 from the module container 210 to the patient 1. Transfer is accomplished using biocompatible fluid (e.g., saline, or other biocompatible fluid) flow through tube 220. Transfer into the patient's body is initiated by gravity feed and then magnetic force control is used to move the module within the patient, via the NMR machine 80 of system 100. The same movement control process is used whether module 10 is inserted into a blood vessel, or other duct or vessel, such as in the urinary duct system, bronchial tubes, glandular ducts, or any other tube or duct in the patient's body.

Figure 5:
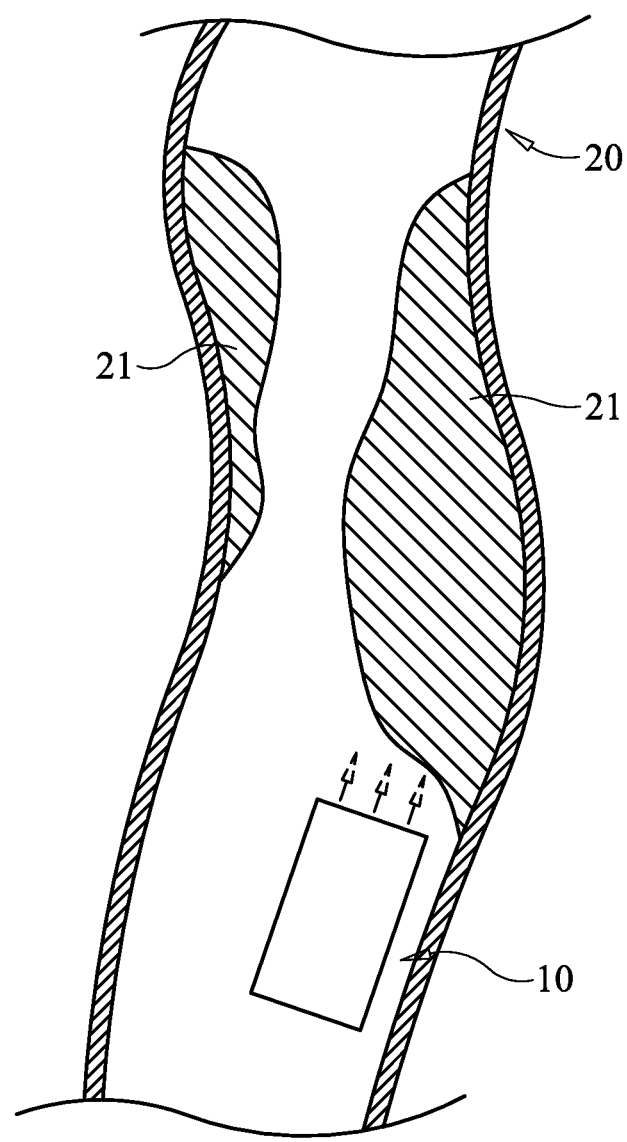
FIG. 5 is an illustration of a vessel in need of clearing or cleaning.

FIG. 5 is an illustration of a vessel 20 in need of clearing or cleaning. The blocking material 21 (e.g., plaque, fatty and/or calcified buildup or other obstruction) is indicated within the vessel 20. The artery (vessel) clearing module 10 is indicated within the vessel.

Figure 6A:
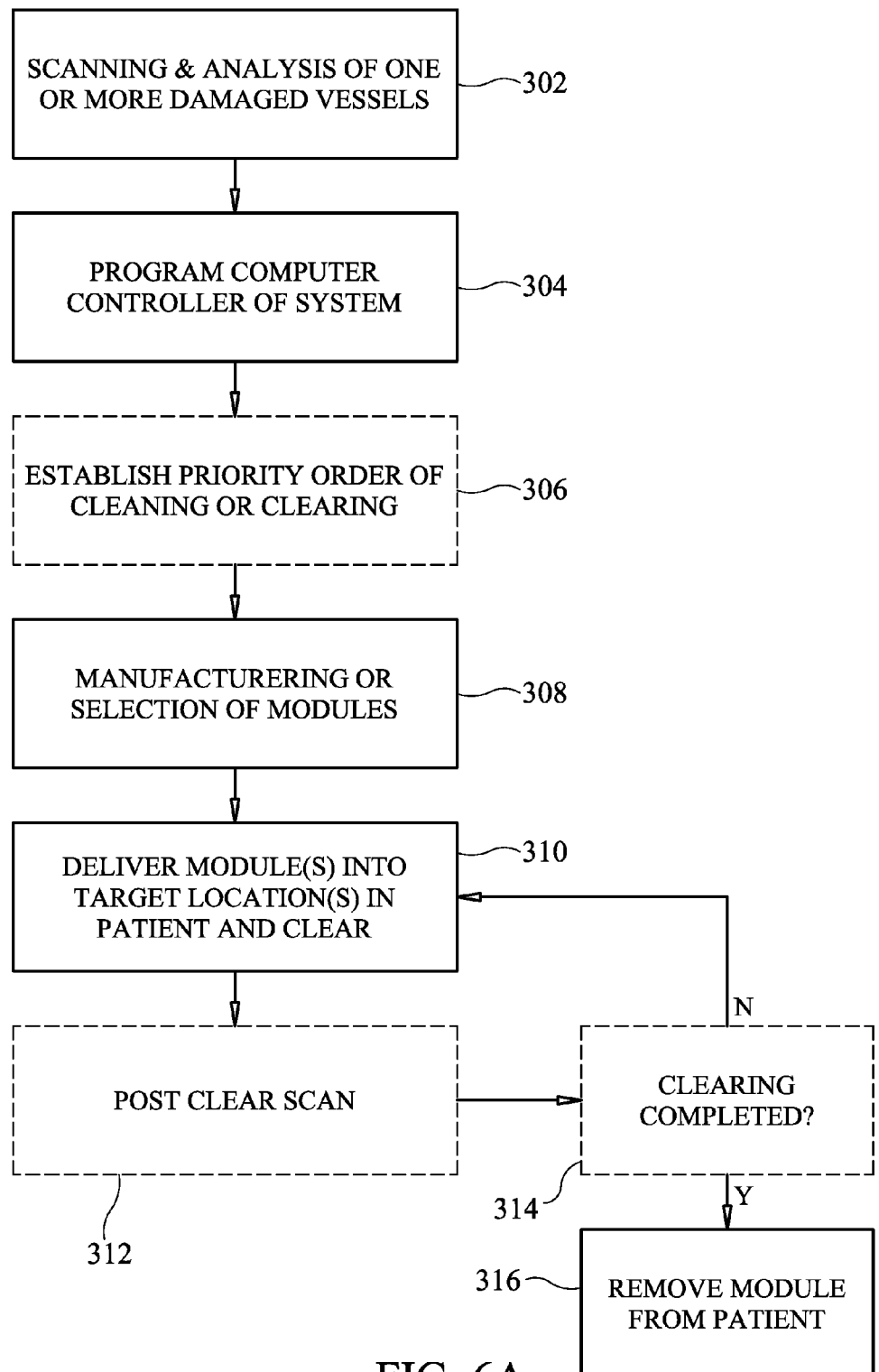
FIG. 6A is a flow chart illustrating events that may occur during a vessel clearing procedure according to an embodiment of the present invention.

FIG. 6A is a flow chart illustrating events that may occur during a vessel clearing procedure according to an embodiment of the present invention. At event 302, scanning and analysis of a patient 1 are conducted. The patient 1 is scanned using CT or MRI technology. The scan and analysis may be conducted on a single vessel only or any number of vessels, up to and including any or all vessels and/or ducts in the patient's body. The results of the scan are analyzed by the administrator of the scanning procedure and/or consulting physicians.

The analysis of one or more vessels is performed to determine the location(s) of a blockage or other obstruction(s) or target location to be treated. This analysis 302 can be performed, for example, by performing a CAT scan of the patient 1, using the CAT scan sub-section 90 of system 100. The exact coordinates of the blockage(s) of the artery (ies) or vein(s) or other vessel(s) in need of restoration are determined, in order to provide a map thereof for reference thereto by NMR sub-section 80 during performance of the delivery and implementation of the module(s) 10.

As a result of the analysis, if one or more obstructed, partially obstructed, damaged or otherwise abnormal vessel/duct is identified that can be treated by one or more modules 10, then the location(s) of the sites to be treated by module (10) are programmed (event 304) into a control computer of system 100, such as at control station 95. The programmed parameters may be for operation on a single vessel using a single module 10, but may include parameters for multiple procedures at multiple target sites using multiple modules 10 which may be of the same, or different sizes, depending upon the diameters and conformations of the vessels/ducts to be treated, as well as the parameters of the obstruction or other tissue to be destroyed. The programming provides a map of a target surgical location of a blockage, partial blockage or other obstruction in a vessel or duct. The map created by the scanning provides coordinates of landmarks within the physiology of the patient, including coordinates of the vessel or duct to be treated and the coordinates of the location of the obstruction(s) that is/are to be the surgical target locations for operation thereon by one or more modules 10. The coordinates of the surgical target location(s), vessel(s) and duct(s) containing the surgical target location(s) and, optionally, any other physiological landmarks that may be useful in navigating the one or more modules 10 within the patient 1 are programmed into a computer controller at event 304, of the target surgical location(s) relative to the map.

Optionally event 306 may be carried out to establish a priority of order in which multiple surgical target locations are treated. This may be accomplished by a surgeon, a medical team, or any other entity with the surgical expertise and sufficient knowledge of these surgical techniques qualifying them to do so. An algorithm used by the controlling computer 95 can use the priority list to ascertain a sequence in which the modules 10 are manufactured and arranged in module container 210. Or a range of different sizes of modules 10 may be pre-manufactured, and the algorithm may be used to select the sizes of pre-manufactured modules 10 that are needed for the procedure(s). The modules 10 are manufactured before they are placed into module container 210. The algorithm may further be used to establish the priority regarding the order of deployment of the modules 10 into the vessels/ducts in need of repair. If there is only one module 10 to be manufactured or selected and implanted or if there is no particular criticality in the order in which a multiplicity of modules 10 are assembled and implanted, then optional event 306 need not be carried out.

At event 308 the one or more modules 10 to be delivered into the patient 1 are manufactured and/or selected. Typically no more than two or three modules 10 are inserted into one entry location during a procedure, without first removing one or more additional modules. Preferably only one module 10 per entry point is inserted. Once all modules 10 needed for the procedure are ready for delivery into the patient 1, the patient 1 is prepared, including inserting tube 220 into a vessel, duct or other tubular tissue through which module(s) 10 can be delivered to the surgical target site(s). There may be more than one tube 220 inserted into more than one vessel, duct or other tubular tissue of the patient 1, depending upon the locations of the surgical target sites, which may determine the starting locations for entry into the patient. The modules 10 are loaded into module container 210 (there may also be multiple module containers 210 when multiple tubes 220 are used to access multiple entry points in the patient 1) in the proper order, if there is one, such as determined at event 306, for example, using any information having been inputted with regard to dimensions of modules 10 needed, as well as priority of movement. Module sizes will vary depending primarily upon the cross-sectional diameter and conformation of the vessel/duct that it is to be delivered into, as measured near the surgical target location, but also including conformational features of vessels/ducts that the module 100 needs to pass through to reach the surgical target area. For example, the width of the module 10 needs to be less than the diameter of the vessel/duct adjacent the surgical target location. The length of the module may need to be varied not only according to the diameter of the vessels/ducts that it is to pass through, but may also be affected by the conformation. For example, the length of a module 10 that needs to traverse a tortuous pathway may need to be shorter than the length of a module 10 that traverses a relatively straight pathway, even though the inside diameter of the vessel adjacent the surgical target area is the same in both cases. For arteries, the module dimensions are typically no greater than about 1.0 cm in length and 0.5 cm in width. Modules may be as small as about 1000 nanometers in length and about 500 nanometers in width, such as for use in capillaries, for example. All sizes within the above two examples are also possible. Modules 10 larger than 1.0 cm in length and 0.5 cm in width can also be manufactured. Each module 10 has a unique identification (ID) code that it can be addressed by, that is unique in that it is different from the identification codes of all other modules 10.

At event 310 the one or more modules 10 are delivered into the patient 1 through one or more vessels or ducts in which one or more conduits 220 have been inserted; and transported to locations adjacent surgical target locations in the body of the patient, respectively. The system 100 guides and controls the modules 10 based on the locations of the modules 10 and the targeted locations of the abnormal, damaged, blocked or diseased vessels, i.e., established as the surgical target sites. The buffer transducer and guide bar 17 keeps the module 10 at safe distances from the vessel walls. The transducers within 17 determine the distance of the module from the vessel walls and regularly feedback this distance information to a predetermined algorithm, the road map which has pre-calculated safe distance values all along the route to the surgical target location. This feedback loop is used to control positioning of the module 10 to ensure that it maintains a safe distance from the walls of the vessel at all times. The guiding is performed by registering the movements of the module 10 with the map to provide precise navigation of the module 10 through the anatomy and to the target surgical location; where the module is remotely operated to treat the material at the surgical target location (for example, to clear a blockage of a vessel, or other treatment).

The operator at the control panel 95 can visually monitor (e.g., on one or more computer monitors 95M) the locations of the modules 10, as well as the surgical target locations, and other related structures and landmarks within the patient (displayed on the map), including, but not limited to the vessel that the module 10 is travelling through. Thus, the operator can continuously (or intermittently) view the locational relationship of each module 10 and the vessel it is currently travelling through, as well as its positional relationship relative to the vessel and surgical target site that it is intended to treat, in real time. The operator can stop or pause the procedure at any time needed via control of the NMR machine 80 and/or control of modules 81, 82 and/or 83. Upon reaching a surgical target site and proper positioning of module 10 adjacent to the surgical target site, X-ray energy is sent from module 82 to X-ray receiving unit 11, X-ray energy is transferred from unit 11 to X-ray conversion unit 12, X-ray energy is converted to photons by X-ray energy conversion unit 12 and sent to intermediate laser beam transmission unit 13, where the photons are organized into a laser beam and transmitted to multiple final beam transmitters 14a in beam length and intensity unit 14. Elements 14a emit laser energy to the surgical target site to destroy (e.g., vaporize or ablate) the material at the surgical target site, e.g., plaque obstructing a vessel or other obstruction, growth, diseased tissue, or other unwanted material. The length of the laser beams emitted is up to, but not exceeding about ten percent of the overall length of the module 10. The amount of energy in the laser beam in terms of Watts depends upon the length of the beam, but is on the order of nano Watts. The intensity, length duration, power and all other variable characteristics of the laser beams emitted by elements 14a are algorithmically controlled by the circuits between the electronic interface 122 and the final beam transmitters 14a, as instructed by instructions received from instruction receiving unit 19, and ultimately by controller 95 and instructions transmission module 83 of system 100. The control may be by an algorithmic voltage oscillator where an electrical signal controls the frequency of the oscillator. The frequency of oscillation can be varied by the applied DC voltage, while modulating signals may also be fed into the voltage controlled oscillator to cause frequency modulation (FM) or phase modulation (PM). A voltage controlled oscillator with digital pulse output may similarly have its repetition rate or pulse width modulated. The laser energy is typically applied in bursts. The module 10 is tracked on the map of the patient's circulatory system (FIG. 5 illustrates a view of beginning a clearing event, where module 10 is positioned adjacent an obstruction 21 and beginning to ablate by application of laser energy thereto) and is advanced further into the vessel as the ablation process continues. Once the module 10 has completed the ablation and eliminated the obstruction, having moved to the distal end of where the obstruction was previously located, the operator at 95 visually observes the movement and completion of the ablation process. Optionally one or CMOS cameras may be provided in module 10 to provide real time video of the obstructions as well as to provide visual feedback of the emitting laser beams and their effect on the obstruction. Otherwise, movement of the module 10 is tracked in relation to the roadmap, guided by a predetermined path to the surgical target area. Also, the operator is aware of the location of the module 10 at all times.

After executing a clearing event 310 on a surgical target (blockage or other obstruction), a scan (e.g., CAT Scan or other visualization) of the target surgical area (similar to the procedure in FIG. 6, event 302, but may be more localized) may be performed to confirm that the module 10 has successfully cleared the blockage/obstruction.

At event 314, if it is determined that the blockage/obstruction has been satisfactorily cleared, then the module is removed from the patient at event 316. If instead, the blockage/obstruction has not been sufficiently or satisfactorily cleared, then processing returns to event 308 where the module repeats application of energy to the blockage/obstruction to affect additional clearing. This loop (314-310-312-314) continues until the blockage/obstruction has been satisfactorily cleared, at which time, the module 10 can be removed from the patient.

After performance of clearing all blockages (or otherwise treating all surgical target sites, such as removing partial obstructions or other unwanted materials), a post-clear scan may optionally be performed at event 312 to confirm successful completion of the procedures, or to inform the operator if one or more modules 10 need to be used to redo a clearing procedure on one or more surgical target areas. If a particular module 10 is needed for a particular surgical target site, but that module 10 has already been previously removed from the patient 1, the module 10 can be reinserted to perform the procedure again.

Figure 6B:
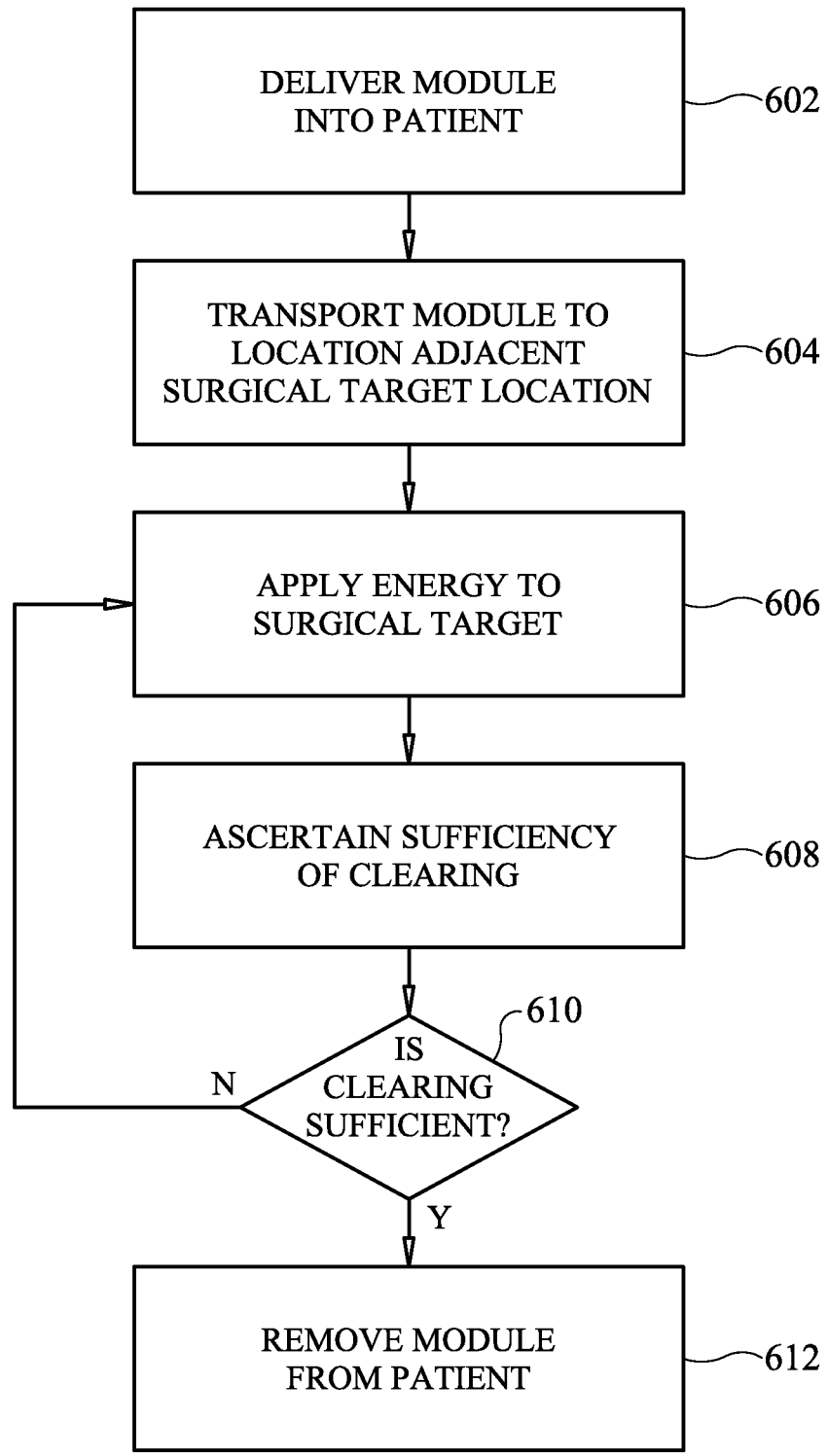
FIG. 6B is a flow chart illustrating events that may occur while performing delivery of one or more devices into a patient, clearing of one or more obstruction, and removal of the one or more devices according to an embodiment of the present invention.

FIG. 6B is a flow chart illustrating events that may occur while performing delivery of one or more devices into a patient, clearing of one or more obstructions, and removal of the one or more devices according to an embodiment of the present invention. At event 602 a module 10 is delivered into a vessel or duct of a patient according to techniques already described herein. At event 604, the module 10 is then transported to a location within a vessel or duct that is immediately adjacent to a surgical target area. Module 10 is driven and guided via NMR machine 80\*\* (i.e., using magnetic forces applied to module 10) to guide the module 10 along a pathway identified by provision and analysis of the CT or MRI scan described above. The NMR machine utilizes the positioning devices 15 and guide bars 17 to guide the module 10 to the surgical target location. Positioning devices/elements 15 ensure the module 10 is aligned with the vessel 20 wall, as they are located at four corners of the module 10 and their positions relative to the vessel 20 wall can be monitored by the master machine 100. Positioning elements 15 may be magnetic, or include a radioactive tracing element, and/or be radiopaque and/or have some other characteristic that allows its position to be traced from outside the patient's body. The NMR machine 80 tracks the movement of the module along the programmed roadmap so the module 10 is maintained in a predetermined position, relative to the vessel walls, along the route to the surgical target area at all times. Safe distances from the vessel walls are predetermined by the algorithm/roadmap and will vary depending upon the size of the module 10 and the inside diameter and conformation (e.g., straight, or relative degree of curvature and tortuosity) of the vessel it is travelling through. In one non-limiting example, a safe distance for a module having a width of 100 nanometers, was in the range of about 10 to about 20 nanometers from the vessel wall. As noted, this can vary considerable depending on the inside diameter of the vessel 20, the conformation of the vessel 20, and the width and length of the module 10. In general, safe distances are typically within the range of about ten to about twenty percent of the width of the module 10, although these safe distances may vary. Feedback information is provided by the buffer transducer within guide bars 17 as to the proximity of the bars 17 to the vessel walls. This feedback is continuously fed back to the NMR machine 80, and NMR machine 80 uses the feedback to maintain the module 10 at a safe distance from the vessel wall as at all times. The buffer transducer(s) may be in the form of ultrasound emitter and receiver, for example.

Once it has been confirmed (by the operator of the control station 95 visually observing, on monitor 95M, the module 10 adjacent the surgical target location) that the module 10 has been accurately placed in a position immediately adjacent the surgical target location and oriented to as to apply energy directly to the surgical target, the position and orientation of the module 10 are then accurately maintained using magnetic forces applied by NMR machine 80, as controlled by continuous feedback provided by positioning elements/devices 15 and bars 17 and destructive energy is applied to the material to be removed at the surgical target location, see event 606.

After completing a session of application of energy at event 606, or alternately during performance of event 606 (monitoring either continuously or intermittently), monitoring is performed at event 608 to ascertain whether and when the surgical target has been sufficiently cleared from the vessel/duct. Monitoring can be performed visually on monitor 95M by the operator of the control station 95 and/or via direct feedback from the module 10, such as may be provided by visualization features such as ultrasonic imaging or other form of onboard imaging. If it is determined at event 610 that the obstruction/blockage has not been sufficiently cleared, then processing returns to event 606 where energy is again applied to the surgical target by the module 10. Loop 610-606-608-610 continues until the obstruction/blockage has been sufficiently cleared. Once the blockage/obstruction has been determined to be sufficiently cleared at event 610, then the module 10 is removed from the patient at event 612.

Figure 7:
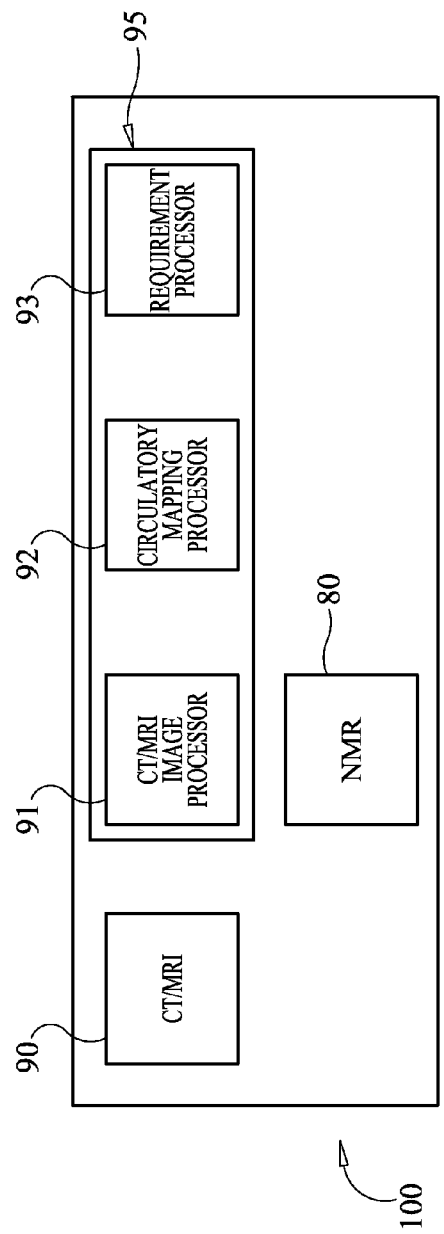
FIG. 7 is a schematic illustration of hardware components included in a system according to an embodiment of the present invention.

FIG. 7 is a schematic illustration of hardware components included in system 100 according to an embodiment of the present invention. Data sent from the CT/MRI section 90 from the clamshell after mapping is sent to the CT/MRI image processor section 91, the circulatory mapping processor 92 and the requirement processor 93 for analysis and programming of the roadmap, requirements and instructions to be executed with the computer 95. The CT/MRI subsystem 90 obtains data for mapping the vessel system to be traversed as well as surgical target location(s). This data is mapped so that coordinates can be relied upon by the NMR subsystem 80 to drive and position the module 10 within the patient 1. The data obtained by the CT/MRI subsystem 90 is processed by the CT/MRI image processor 91 and the image-processed data is transferred to the circulatory mapping processor 92. Processor 92 further processes the image-processed data to output a detailed map of the vessel system to be traversed and surgical target location(s) all mapped to coordinates relative to the patient 1. The requirement processor then generates an algorithm and provides it for use by the NMR subsystem 80 to reference for guiding and positioning module 10.

Figure 8:
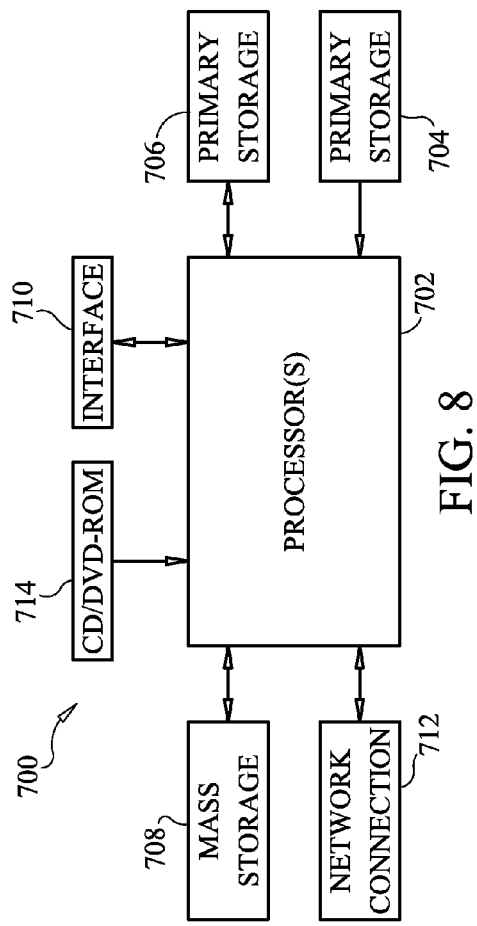
FIG. 8 is a block diagram of a computer system that may be implemented in a system according to an embodiment of the present invention.

FIG. 8 is a block diagram of a computer system that may be implemented in system 100 according to an embodiment of the present invention. This figure represents a typical computer system, components of which, or all of which may be employed in system 100. The computer system 700 includes any number of processors 702 (also referred to as central processing units, or CPUs, and, for example, which may be employed in the computer controller 95 of system 100, as well as one or more sub-sections described) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers, any of which may be included in console 95, for example. Interface 710 may include interfaces to NMR 80 and CT/MRI 90 sections, and the like. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A clearing module comprising:
 a main body configured and dimensioned to be received within a vessel or duct of a patient, adjacent a surgical target area in the patient, said main body including:
 an instruction receiving unit configured to receive wireless instructions from an instruction transmitter located outside the patient's body while said module is located inside of the patient's body;
 a positioning element configured to be monitored by a system external of the patient's body while said positioning element is inside the patient's body; and
 a destructive energy emitter configured to emit destructive energy from said module toward the surgical target area according to instructions received from said instructions receiving unit;
 wherein said module is configured to wirelessly receive non-destructive energy from outside the body and convert said non-destructive energy to said destructive energy;
 wherein said non-destructive energy comprises X-ray energy;
 wherein said destructive energy comprises laser energy.

2. The module of claim 1, further comprising a non-destructive energy receiving unit configured to wirelessly receive said non-destructive energy from an energy transmitting unit located outside of the patient's body, while said non-destructive energy receiving unit is located inside of the patient's body.

3. The module of claim 2, comprising an energy conversion unit configured to receive said non-destructive energy from said non-destructive energy receiving unit and further configured to convert said non-destructive energy to another modality of energy.

4. The module of claim 3, further comprising a destructive energy transmission unit configured to receive said another modality of energy and convert said another modality of energy into said destructive energy.

5. The module of claim 4, wherein said destructive energy emitter is configured to receive said destructive energy from said destructive energy transmission unit and emit said destructive energy from said module toward said surgical target area.

6. The module of claim 1, further comprising a guide bar and communication interface configured to transfer instructions from said instruction receiving unit to other locations in said main body.

7. A system for treating a patient, said system comprising:
 a control subsystem located externally of the body of the patient, said control subsystem including a non-destructive energy transmitter; and
 a clearing module configured and dimensioned to be received within a vessel or duct of the body of the patient; said clearing module including:
 a positioning element configured to be monitored by said sub-system external of the patient's body while said positioning element is inside the patient's body; and
 a non-destructive energy receiving unit configured to receive non-destructive energy from said non-destructive energy transmitter located outside of the patient's body while said non-destructive energy receiving unit is located inside of the patient's body; and
 a destructive energy emitter configured to emit destructive energy;

wherein said control subsystem is configured to drive and guide said clearing module along a pathway inside of the patient to a predetermined location adjacent a surgical target;

wherein said non-destructive energy comprises X-ray energy;

wherein said destructive energy comprises laser energy.

8. The system of claim 7, wherein said control subsystem includes a nuclear magnetic resonance (NMR) machine configured to drive and guide said clearing module along said pathway inside of the patient to the predetermined location adjacent the surgical target.

9. The system of claim 7, wherein said clearing module is configured to convert said non-destructive energy received by said non-destructive energy receiving unit to destructive energy.

10. The system of claim 9, wherein said clearing module is configured to emit said destructive energy from said module toward the surgical target.

11. The system of claim 7, wherein said control subsystem includes a wireless instruction transmitter and said module includes an instruction receiving unit configured to receive wireless instructions from said wireless instruction transmitter located outside the patient's body while said module is located inside of the patient's body.

12. The system of claim 10, wherein said control subsystem includes a wireless instruction transmitter and said module includes an instruction receiving unit configured to receive wireless instructions from said wireless instruction transmitter located outside the patient's body while said module is located inside of the patient's body; and wherein instructions received by said instruction receiving unit include instructions for controlling said conversion of non-destructive energy to destructive energy.

13. The system of claim 10, wherein said control subsystem includes a wireless instruction transmitter and said module includes an instruction receiving unit configured to receive wireless instructions from said wireless instruction transmitter located outside the patient's body while said module is located inside of the patient's body; and wherein instructions received by said instruction receiving unit include instructions for emitting said destructive energy and for controlling at least one characteristic of said destructive energy that is emitted.

14. A clearing module comprising:

a main body configured and dimensioned to be received within a vessel or duct of a patient, adjacent a surgical target area in the patient, said main body including:

an instruction receiving unit configured to receive wireless instructions from a first type of energy received wirelessly from an instruction transmitter located outside the patient's body while said module is located inside of the patient's body;

a positioning element configured to be monitored by a system external of the patient's body while said positioning element is inside the patient's body;

a non-destructive energy receiving unit configured to wirelessly receive a second type of energy from an energy transmitting unit located outside of the patient's body, while said non-destructive energy receiving unit is located inside of the patient's body, wherein said second type of energy is different from said first type of energy and is non-destructive energy; and a destructive energy emitter configured to emit destructive energy from said module toward the surgical target area according to instructions received from said instructions receiving unit; wherein said module is configured to convert said non-destructive energy to said destructive energy within said module.

15. The module of claim 14, wherein said first type of energy comprises RF energy, and said second type of energy comprises energy having a frequency outside a frequency range of RF energy.

16. The module of claim 14, wherein said second type of energy comprises X-ray energy, and said first type of energy comprises energy having a frequency outside a frequency range of X-ray energy.

17. The module of claim 14, further comprising a non-destructive energy conversion unit configured to receive said non-destructive energy from said non-destructive energy unit, convert said non-destructive energy to said destructive energy, and output said destructive energy to a destructive energy unit.

18. The module of claim 17, wherein said destructive energy unit channels and transfers said destructive energy to said destructive energy emitter.

* * * * *

UNITED STATES PATENT AND TRADEMARK OFFICE
CERTIFICATE OF CORRECTION

| | | |
|---|---|---|
| PATENT NO. | : 8,663,209 B2 | Page 1 of 1 |
| APPLICATION NO. | : 13/356884 | |
| DATED | : March 4, 2014 | |
| INVENTOR(S) | : Zurn | |

It is certified that error appears in the above-identified patent and that said Letters Patent is hereby corrected as shown below:

In the Specification,

Column 16, Line 7, please delete "to more" and insert --to move--.

Signed and Sealed this
Thirtieth Day of June, 2015

Michelle K. Lee
*Director of the United States Patent and Trademark Office*